(12) United States Patent
Rubinstein et al.

(10) Patent No.: US 7,868,154 B2
(45) Date of Patent: Jan. 11, 2011

(54) PROMOTER TO IL-18BP, ITS PREPARATION AND USE

(75) Inventors: Menachem Rubinstein, Rehovot (IL); Daniela Novick, Rehovot (IL); Vladimir Hurgin, Ashdod (IL)

(73) Assignee: Yeda Research and Development Co. Ltd. IL (US)

( * ) Notice: Subject to any disclaimer, the term of this patent is extended or adjusted under 35 U.S.C. 154(b) by 340 days.

(21) Appl. No.: 10/530,963

(22) PCT Filed: Oct. 9, 2003

(86) PCT No.: PCT/IL03/00815

§ 371 (c)(1),
(2), (4) Date: Jun. 21, 2005

(87) PCT Pub. No.: WO2004/033694

PCT Pub. Date: Apr. 22, 2004

(65) Prior Publication Data

US 2006/0239984 A1 Oct. 26, 2006

(30) Foreign Application Priority Data

Oct. 10, 2002 (IL) .................................. 152232

(51) Int. Cl.
| | |
|---|---|
| C12N 15/00 | (2006.01) |
| C12N 5/00 | (2006.01) |
| C12N 15/09 | (2006.01) |
| C12N 15/11 | (2006.01) |
| C12N 15/63 | (2006.01) |
| C12N 15/67 | (2006.01) |

(52) U.S. Cl. .................. 536/24.1; 536/23.1; 435/320.1; 435/69.1; 435/325

(58) Field of Classification Search ........................ None
See application file for complete search history.

(56) References Cited

U.S. PATENT DOCUMENTS 4,966,843 A * 10/1990 McCormick et al. ...... 435/69.51

FOREIGN PATENT DOCUMENTS

| EP | 0 546 333 A1 * | 6/1993 |
|---|---|---|
| WO | WO 99 09063 A | 2/1999 |

OTHER PUBLICATIONS

Osoegawa et al. (2001) Genome Res. 11:483-496.*
Guan et al. (1995) J. Biol. Chem. 270:21958-21965.*
Entrez Nucleotide Database entry for Accession No. AP000719, http://www.ncbi.nlm.nih.gov/entrez/viewer.fcgi?db=nuccore&id=13094220, sequence published prior to Jul. 23, 2002.*
Entrez Nucleotide Database entry for Accession No. AF110798, http://www.ncbi.nlm.nih.gov/entrez/viewer.fcgi?db=nuccore&id=4324923, published Mar. 3, 1999, downloaded Oct. 29, 2007.*
Rubanyi (2001) Mol. Aspects Med. 22:113-142.*
Ross et al. (1996) Human gene Therapy 7:1781-1790.*
Eck et al. (1996) Goodman & Gilman's The Pharmacological Basis of Therapeutics, 9th Edition, Chapter 5, McGraw-Hill, NY.*
Marshall (1995) Science 269:1050-1055.*
Verma et al. (1997) Nature 389:239-242.*
Pance et al, A repressor in the proximal human inducible nitric oxide synthase promoter modulates transcriptional activation, FASEB J. (Feb. 25, 2002), pp. 631-633.*
Novick, D. et al. Interleukin-18 Binding Protein: A Novel Modulator of the TH1 Cytokine Response; Immunity, *Cell Press, US, Online!*, vol. 10, No. 1, Jan. 1999, pp. 127-136.
Kim, S-H et al. Structural Requirements of Six Naturally Occurring Isoforms of the IL-18 Binding Protein to Inhibit IL-18, *Proceedings of the National Academy of Sciences of USA, National Academy of Science*. Washington, US, vol. 97, No. 3, Feb. 1, 2000, pp. 1190-1195.
Database EMBL 'Online! Nov. 4, 2002 Novick: "IL18 binding protein" retrieved from EBI Database accession No. BD074754.
Database EMBL 'Online! Nov. 4, 2002 Novick: "IL18 binding protein" retrieved from EBI Database accession No. BD074752.
Hurgin, Vladimir et al. The promoter of IL-18 binding protein: Activation by an IFN-gamma-induced complex of IFN regulatory factor 1 and CCAAT/enchancer binding protein beta. *Proceedings of the National Academy of Sciences of the United States*, vol. 99, No. 26, Dec. 24, 2002, pp. 16957-16962.
Hurgin, Vladimir et al. Transcriptional regulation of IL-18 binding protein gene expression, *Journal of Interferon and Cytokine Research*, vol. 24, No. Supplement 1, 2001, p. S.73.
Banner I, et al. "Comparison of trans-dominant inhibitory mutant human immunodeficiency virus type 1 genes expressed by retroviral vectors in human T lymphocytes." J Virol. Jun. 1993;67(6):3199-207.
Boshart M, et al. "A very strong enhancer is located upstream of an immediate early gene of human cytomegalovirus." Cell. Jun. 1985;41(2):521-30.
Bregni M, et al. "Human peripheral blood hematopoietic progenitors are optimal targets of retroviral-mediated gene transfer." Blood. Sep. 15, 1992;80(6):1418-22.
Brinster Rl, et al. "Somatic expression of herpes thymidine kinase in mice following injection of a fusion gene into eggs." Cell. Nov. 1981;27(1 Pt 2):223-31.
Cassel A, et al. "Retroviral-mediated gene transfer into CD34-enriched human peripheral blood stem cells." Exp Hematol. Apr. 1993;21(4):585-91.
Chao NJ, et al. "Granulocyte colony-stimulating factor "mobilized" peripheral blood progenitor cells accelerate granulocyte and platelet recovery after high-dose chemotherapy." Blood. Apr. 15, 1993;81(8):2031-5.
Chen JD, et al. "Inactivation of HIV-1 chemokine co-receptor CXCR-4 by a novel intrakine strategy." Nature Med. Oct. 1997;3(10):1110-6.
Costantini F, and Lacy E. "Introduction of a rabbit beta-globin gene into the mouse germ line." Nature. Nov. 5, 1981;294:92-4.
Couture LA, and Stinchcomb DT. "Anti-gene therapy: the use of ribozymes to inhibit gene function." Trends Genet. Dec. 1996;12(12):510-5.

(Continued)

*Primary Examiner*—Maria Marvich
(74) *Attorney, Agent, or Firm*—Nixon Peabody LLP

(57) ABSTRACT

The present invention relates to the promoter of interleukin-18 binding protein (IL-18BP), to its preparation and use.

32 Claims, 8 Drawing Sheets

OTHER PUBLICATIONS

Dignam JD, et al. "Accurate transcription initiation by RNA polymerase II in a soluble extract from isolated mammalian nuclei." Nucleic Acids Res. Mar. 11, 1983;11(5):1475-89.

Dijkema R, et al. "Cloning and expression of the chromosomal immune interferon gene of the rat." EMBO J. Mar. 1985;4(3):761-7.

Dunbar CE, et al. "Retrovirally marked CD34-enriched peripheral blood and bone marrow cells contribute to long-term engraftment after autologous transplantation." Blood. Jun. 1, 1995;85(11):3048-57.

Dynan WS, and Tjian R. "Control of eukaryotic messenger RNA synthesis by sequence-specific DNA-binding proteins." Nature. Aug. 29-Sep. 4, 1985;316(6031):774-8.

Dynan WS. "Modularity in promoters and enhancers." Cell. 1989 Jul. 14;58(1):1-4.

Fletcher C, et al. "Purification and characterization of OTF-1, a transcription factor regulating cell cycle expression of a human histone H2b gene." Cell. Dec. 4, 1987;51(5)773-81.

Fried M, and Crothers DM. "Equilibria and kinetics of lac repressor-operator interactions by polyacrylamide gel electrophoresis." Nucleic Acids Res. Dec. 11, 1981;9(23):6505-25.

Gale RP, et al. "Blood stem cell transplants come of age." Bone Marrow Transplant. Mar. 1992;9(3):151-5.

Gordon S, and Werb Z. "Secretion of macrophage neutral proteinase is enhanced by colchicine." Proc Natl Acad Sci U S A. Mar. 1976;73(3):872-6.

Gorman CM, et al. "The Rous sarcoma virus long terminal repeat is a strong promoter when introduced into a variety of eukaryotic cells by DNA-mediated transfection." Proc Natl Acad Sci U S A. Nov. 1982;79(22):6777-81.

Hao QL, et al. "A functional comparison of CD34 + CD38- cells in cord blood and bone marrow." Blood. Nov. 15, 1995;86(10):3745-53.

Harbers K, et al. "Microinjection of cloned retroviral genomes into mouse zygotes: integration and expression in the animal." Nature. Oct. 15, 1981;293:540-2.

Henon PR, et al. "Comparison of hematopoietic and immune recovery after autologous bone marrow or blood stem cell transplants." Bone Marrow Transplant. Apr. 1992;9(4):285-91.

Herzog RW, et al. "Stable gene transfer and expression of human blood coagulation factor IX after intramuscular injection of recombinant adeno-associated virus." Proc Natl Acad Sci U S A. May 27, 1997;27;94(11):5804-9.

Junker U, et al. "Hematopoietic potential and retroviral transduction of CD34+ Thy-1+ peripheral blood stem cells from asymptomatic human immunodeficiency virus type-1-infected individuals mobilized with granulocyte colony-stimulating factor." Blood. Jun. 15, 1997;89(12):4299-306.

Kearns WG, et al. "Recombinant adeno-associated virus (AAV-CFTR) vectors do not integrate in a site-specific fashion in an immortalized epithelial cell line." Gene Ther. Sep. 1996;3(9):748-55.

Kohn DB, et al. "A clinical trial of retroviral-mediated transfer of a rev-responsive element decoy gene into CD34(+) cells from the bone marrow of human immunodeficiency virus-1-infected children." Blood. Jul. 1, 1999;94(1):368-71.

Lee SW, et al. "Inhibition of human immunodeficiency virus type 1 in human T cells by a potent Rev response element decoy consisting of the 13-nucleotide minimal Rev-binding domain." J Virol. Dec. 1994;68(12):8254-64.

Lotti F, et al. "Transcriptional targeting of lentiviral vectors by long terminal repeat enhancer replacement." J Virol. Apr. 2002;76(8):3996-4007.

Malim MH, et al. "Functional dissection of the HIV-1 Rev trans-activator—derivation of a trans-dominant repressor of Rev function." Cell. Jul. 14, 1989;58(1)205-14.

Maniatis T, et al. "Regulation of inducible and tissue-specific gene expression." Science. Jun. 5, 1987;236:1237-45.

Marasco WA. "Intrabodies: turning the humoral immune system outside in for intracellular immunization." Gene Ther. Jan. 1997;4(1):11-5.

Mcknight S, and Tjian R. "Transcriptional selectivity of viral genes in mammalian cells." Cell. Sep. 12, 1986;46 (6):795-805.

Miyoshi H, et al. "Transduction of human CD34+ cells that mediate long-term engraftment of NOD/SCID mice by HIV vectors." Science. Jan. 29, 1999;283:682-6.

Moritz T, et al. "Human cord blood cells as targets for gene transfer: potential use in genetic therapies of severe combined immunodeficiency disease." J Exp Med. Aug. 1, 1993;178(2):529-36.

Mühl H, et al. "Interferon-gamma mediates gene expression of IL-18 binding protein in nonleukocytic cells." Biochem Biophys Res Commun. Jan. 27, 2000;267(3):960-3.

Murphy JE, et al. "Long-term correction of obesity and diabetes in genetically obese mice by a single intramuscular injection of recombinant adeno-associated virus encoding mouse leptin." Proc Natl Acad Sci U S A. Dec. 9, 1997;94 (25):13921-6.

Neighbors M, et al. "A critical role for interleukin 18 in primary and memory effector responses to Listeria monocytogenes that extends beyond its effects on Interferon gamma production." J Exp Med. Aug. 6, 2001;194 (3):343-54.

Novick D, et al. "Interleukin-18 binding protein: a novel modulator of the Th1 cytokine response." Immunity. Jan. 1999;10(1):127-36.

Novick D, et al. "A novel IL-18BP ELISA shows elevated serum IL-18BP in sepsis and extensive decrease of free IL-18." Cytokine. Jun. 21, 2001;14(6):334-42.

Palmiter RD, and Brinster RL. "Germ-line transformation of mice." Annu Rev Genet. 1986;20:465-99.

Revzin A. "Gel electrophoresis assays for DNA-protein interactions." Biotechniques. Apr. 1989;7(4):346-55.

Sassone-Corsi, P. & Borrelli, E., "Transcriptional regulation by trans-acting factors." Trends in Genetics vol. 2, 1986, pp. 215-219.

Scheidereit C, et al. "Identification and purification of a human lymphoid-specific octamer-binding protein (OTF-2) that activates transcription of an immunoglobulin promoter in vitro." Cell. Dec. 4, 1987;51(5):783-93.

Slobod KS, et al. "Mobilization of CD34+ progenitor cells by granulocyte colony-stimulating factor in human immunodeficiency virus type 1-infected adults." Blood. Nov. 1, 1996;88(9):3329-35.

Snyder RO, et al. "Persistent and therapeutic concentrations of human factor IX in mice after hepatic gene transfer of recombinant AAV vectors." Nature Genet. Jul. 1997; 16(3):270-6.

Snyder RO, et al. "Correction of hemophilia B in canine and murine models using recombinant adeno-associated viral vectors." Nature Med. Jan. 1999;5(1):64-70.

Song S, et al. "Sustained secretion of human alpha-1-antitrypsin from murine muscle transduced with adeno-associated virus vectors." Proc Natl Acad Sci U S A. Nov. 24, 1998;95(24):14384-8.

Sullenger BA, et al. "Overexpression of TAR sequences renders cells resistant to human immunodeficiency virus replication." Cell. Nov. 2, 1990;63(3):601-8.

Veres G, et al. "Intracellular expression of RNA transcripts complementary to the human immunodeficiency virus type 1 gag gene inhibits viral replication in human CD4+ lymphocytes." J Virol. Dec. 1996;70(12):8792-800.

Verma IM, and Somia N. "Gene therapy—promises, problems and prospects." Nature. Sep. 18, 1997;389:239-42.

Voss, D., et al., "The role of enhancers in the regulation of cell-type-specific transcriptional control." Trends Biochem. 11, 287-289 (1986).

Wagner EF, et al. "The human beta-globin gene and a functional viral thymidine kinase gene in developing mice." Proc Natl Acad Sci U S A. Aug. 1981;78(8):5016-20.

Wang L, et al. "Sustained correction of bleeding disorder in hemophilia B mice by gene therapy." Proc Natl Acad Sci U S A. Mar. 30, 1999;96(7):3906-10.

Xiao W, et al. "Adeno-associated virus as a vector for liver-directed gene therapy." J Virol. Dec. 1998;72(12):10222-6.

Zecchina G, et al. "Interleukin-18 binding protein in acute graft versus host disease and engraftment following allogeneic peripheral blood stem cell transplants." J Hematother Stem Cell Res. Dec. 2001;10(6):769-76.

Zhou C, et al. "Inhibition of HIV-1 in human T-lymphocytes by retrovirally transduced anti-tat and rev hammerhead ribozymes." Gene. Nov. 4, 1994;149(1):33-9.

Zwiebel JA et al. "High-level recombinant gene expression in rabbit endothelial cells transduced by retroviral vectors." Science. Jan. 13, 1989;243:220-2.

* cited by examiner

SEQUENCE LISTING

```
<160> NUMBER OF SEQ ID NOS: 5

<210> SEQ ID NO 1
<211> LENGTH: 1272
<212> TYPE: DNA
<213> ORGANISM: Homo sapiens

<400> SEQUENCE: 1
catgaactag acacctagag aagaaggatg tgacttgtag tatcctatgt ctaaattagg      60
aatatgaatc tggtttttct acaagaagtt tgagatcaca gctgactgtg ttcctgatgc     120
atccaccaaa cccagttcca tctgtgggcc tccctggctc tgtcaccagc cgttgcaccc     180
tcccaatcac aggagtcaca aacctcagac atgcagctcc tgtccacact taatatatgc     240
atgcattgga tcacccagcc ctggtctttc tgcctccatg gataactgca tgaccctgag     300
agaaaacctc cttagattta gcatcctagg ttcctcacac gcctcaccct gaatcctggc     360
cctcccgcag ccccagcgcc atttgtccca tcagtgacaa gattcatatt ctgatgtaga     420
ctctgttgcc agagccagtg ttgagccagt ccgcctcttc cccgggaagt gcctgccctt     480
ccctcctgtt agggttggct ctcgagcttg tgtgccagtt cctgggttgg ccgtgagagt     540
tctacagaca aggaggaagt gctctcggtg tatttcctgt ggtgggttca cacgcagcta     600
gacacagcta acttgagtct tggagctcct agagggaagc ttctggaaag gaaggctctt     660
caggacctct taggagccag gtaggagtct gggactacta gtgaacctag acctgtggct     720
ctggccagag gggctaggat gagagacaga gggtgtgatg tgggtgctg ggagatgtag      780 ccgaccttgg ggctggtggc tggggagtg ggtagcctgg gaaaggccag gatgtggacg      840
gactggtatg gcattgagcc tgaagtggtc caacttgggg ttccccagtg cctaggaaag    900
ttgtcccctt gaatgtcagt gtgaaggtga aggaggaagc agatgcctgt tcatatggaa     960
acaaagacct ggctgtgaag aggggaggcg gacaccaaag tcctgacact tgggcgggac    1020
agaattgatc tgtgagagac tcatctagtt catacccctag gtgaccctgg gggtggcatg   1080
```

| | |
|---|---|
| ggggtagatt agagatccca gtctggtatc ctctggagag taggagtccc aggagctgaa | 1140 |
| ggtttctggc cactgaactt tggctaaagc agaggtgtca cagctgctca agattccctg | 1200 |
| gttaaaaagt gaaagtgaaa tagagggtcg gggcagtgct ttcccagaag gattgctcgg | 1260 |
| catcctgccc tt | 1272 |

<210> SEQ ID NO 2
<211> LENGTH: 634
<212> TYPE: DNA
<213> ORGANISM: Homo sapiens

<400> SEQUENCE: 2

| | |
|---|---|
| gcttctggaa aggaaggctc ttcaggacct cttaggagcc aggtaggagt ctgggactac | 60 |
| tagtgaacct agacctgtgg ctctggccag aggggctagg atgagagaca gagggtgtga | 120 |
| tggtgggtgc tgggagatgt agccgacctt ggggctggtg gctgggggag tgggtagcct | 180 |
| gggaaaggcc aggatgtgga cggactggta tggcattgag cctgaagtgg tccaacttgg | 240 |
| ggttccccag tgcctaggaa agttgtcccc ttgaatgtca gtgtgaaggt gaaggaggaa | 300 |
| gcagatgcct gttcatatgg aaacaaagac ctggctgtga agaggggagg cggacaccaa | 360 |
| agtcctgaca cttgggcggg acagaattga tctgtgagag actcatctag ttcataccct | 420 |
| aggtgacccT ggggtggca tggggtaga ttagagatcc cagtctggta tcctctggag | 480 |
| agtaggagtc ccaggagctg aaggtttctg ccactgaac tttggctaaa gcagaggtgt | 540 |
| cacagctgct caagattccc tggttaaaaa gtgaaagtga atagagggt cggggcagtg | 600 |
| ctttcccaga aggattgctc ggcatcctgc cctt | 634 |

<210> SEQ ID NO 3
<211> LENGTH: 122
<212> TYPE: DNA
<213> ORGANISM: Homo sapiens

<400> SEQUENCE: 3

| | |
|---|---|
| cactgaactt tggctaaagc agaggtgtca cagctgctca agattccctg gttaaaaagt | 60 |
| gaaagtgaaa tagagggtcg gggcagtgct ttcccagaag gattgctcgg catcctgccc | 120 |
| tt | 122 |

<210> SEQ ID NO 4
<211> LENGTH: 1061
<212> TYPE: DNA
<213> ORGANISM: Homo sapiens

<400> SEQUENCE: 4

| | |
|---|---|
| tgcagctcct gtccacactt aatatatgca tgcattggat cacccagccc tggtctttct | 60 |
| gcctccatgg ataactgcat gaccctgaga gaaaacctcc ttagatttag catcctaggt | 120 |
| tcctcacacg cctcaccctg aatcctggcc ctcccgcagc cccagcgcca tttgtcccat | 180 |
| cagtgacaag attcatattc tgatgtagac tctgttgcca gagccagtgt tgagccagtc | 240 |
| cgcctcttcc ccgggaagtg cctgcccttc cctcctgtta gggttggctc tcgagcttgt | 300 |
| gtgccagttc ctgggttggc cgtgagagtt ctacagacaa ggaggaagtg ctctcggtgt | 360 |
| atttcctgtg gtgggttcac acgcagctag acacagctaa cttgagtctt ggagctccta | 420 |
| gagggaagct tctggaaagg aaggctcttc aggacctctt aggagccagg taggagtctg | 480 |
| ggactactag tgaacctaga cctgtggctc tggccagagg ggctaggatg agagacagag | 540 |
| ggtgtgatgg tgggtgctgg gagatgtagc cgaccttggg gctggtggct ggggagtgg | 600 |

```
gtagcctggg aaaggccagg atgtggacgg actggtatgg cattgagcct gaagtggtcc      660
aacttggggt tccccagtgc ctaggaaagt tgtccccttg aatgtcagtg tgaaggtgaa      720
ggaggaagca gatgcctgtt catatggaaa caaagacctg gctgtgaaga ggggaggcgg      780
acaccaaagt cctgacactt gggcgggaca gaattgatct gtgagagact catctagttc      840 atacccctagg tgaccctggg ggtggcatgg gggtagatta gagatcccag tctggtatcc     900
tctggagagt aggagtccca ggagctgaag gtttctggcc actgaacttt ggctaaagca      960
gaggtgtcac agctgctcaa gattccctgg ttaaaaagtg aaagtgaaat agagggtcgg     1020
ggcagtgctt tcccagaagg attgctcggc atcctgccct t                        1061

<210> SEQ ID NO 5
<211> LENGTH: 51
<212> TYPE: DNA
<213> ORGANISM: Homo sapiens

<400> SEQUENCE: 5
cccagaagca gctctggtgc tgaagagagc actgcctccc tgtgtgactg g               51
```

PROMOTER TO IL-18BP, ITS PREPARATION AND USE

CROSS-REFERENCE TO RELATED APPLICATIONS

This application is the U.S. National Phase Entry Under 35 U.S.C. §371 of International Application No. PCT/2003/000815, filed Oct. 9, 2003, which designated the U.S., and which claimed benefit under 35 U.S.C. 119 of the Israeli Patent Application No. 152232, filed in English language on 10 Oct. 2002.

FIELD OF THE INVENTION

The present invention relates to the promoter of interleukin-18 binding protein (IL-18BP), to its preparation and use.

BACKGROUND OF THE INVENTION

Cytokine binding proteins (soluble cytokine receptors) are usually the extracellular ligand binding domains of their respective cell surface cytokine receptors. They are produced either by alternative splicing or by proteolytic cleavage of the cell surface receptor. These soluble receptors have been described in the past: for example, the soluble receptors for IL-6 and IFNγ (Novick et al. 1989), TNF (Engelmann et al. 1989 and Engelmann et al. 1990), IL-1 and IL-4 (Maliszewski et al. 1990) and IFNα/β (Novick et al. 1994, Novick et al. 1992). One cytokine-binding protein, named osteoprotegerin (OPG, also known as osteoclast inhibitory factor—OCIF), a member of the TNFR/Fas family, appears to be the first example of a soluble receptor that exists only as a secreted protein (Anderson et al. 1997, Simonet et al. 997, Yasuda et al. 1998).

An interleukin-18 binding protein (IL-18BP) was affinity purified, on an IL-18 column, from urine (Novick et al. 1999). IL-18BP abolishes IL-18 induction of IFNγy, and IL-18 activation of NF-kB in vitro. In addition, IL-18-BP inhibits induction of IFNγ in mice injected with LPS. The IL-18BP gene was localized to the human chromosome 11, and no exon coding for a transmembrane domain could be found in the 8.3 kb genomic sequence comprising the IL-18BP gene. Four isoforms of IL-18BP generated by alternative mRNA splicing have been found in humans so far. They were designated IL-18BP a, b, c, and d, all sharing the same N-terminus and differing in the C-terminus (Novick et al 1999). These isoforms vary in their ability to bind IL-18 (Kim et al. 2000). Of the four, human IL-18BP (hIL-18BP) isoforms a and c are known to have a neutralizing capacity for IL-18. The most abundant IL-18BP isoform, the spliced variant isoform a, exhibits a high affinity for IL-18 with a rapid on-rate and a slow off-rate, and a dissociation constant (Kd) of approximately 0.4 nM (Kim et al. 2000). IL-18BP is constitutively expressed in the spleen (Novick 1999), and circulates at plasma concentrations of 2.5 ng/ml (Novick et al. 2001). The residues involved in the interaction of IL-18 with IL-18BP have been described through the use of computer modelling (Kim et al. 2000) and based on the interaction between the similar protein IL-1β with the IL-1R type I (Vigers et al. 1997). According to the model of IL-18 binding to the IL18BP, the Glu residue at position 42 and Lys residue at position 89 of IL-18 have been proposed to bind to Lys-130 and Glu-114 in IL-18BP, respectively (Kim et al. 2000).

As mentioned, IL-18 induces IFNγ which, in turn, was recently reported to induce IL-18BPa mRNA generation in vitro (Muhl et al 2000). Therefore, IL-18BPa could serve as a "shut off" signal, terminating the inflammatory response.

IL-18BP is significantly homologous to a family of proteins encoded by several Poxviruses (Novick et al. 1999, Xiang and Moss 1999). Inhibition of IL-18 by this putative viral IL-18BP may attenuate the inflammatory antiviral Th1 response. Serum IL 18BP is significantly elevated in sepsis, indicating its role in regulating immune responses in vivo (Novick et al. 2001). Indeed, IL-18BP is induced by IFNγ in various cells, suggesting that it serves as a negative feedback inhibitor of the IL-18-mediated immune response (Mughl et al. 2000)

Preliminary results indicate that IL-18BP mRNA is detected in leukocytes, colon, small intestine, prostate and particularly in spleen cells (Novick et al. 1999). The component cells of the spleen consist of macrophages, lymphocytes, and plasma cells with additional cells derived from the circulation.

The activity of elements that control transcription, promoter and enhancers vary considerably among different cell types. Promoters and enhancers consist of short arrays of DNA sequences that interact specifically with cellular proteins involved in transcription (reviewed in Dynan and Tjian 1985, McKnight and Tjian 1986, Sassone-Corsi and Borreli 1986 and Maniatis et al 1987). The combination of different recognition sequences and the amounts of the cognate transcription factors determine efficiency with which a given gene is transcribed in a particular cell type. Many eukaryotic promoters contain two types of recognition sequences: the TATA box and the upstream promoter elements. The TATA box, located 25-30 bp upstreaqm of the transcription initiation site, is thought to be involved in directing RNA polymerase II to begin RNA synthesis at the correct site. In contrast, the upstream promoter elements determine the rate at which transcription is initiated. Enhancer elements can stimulate transcription up to 1000-fold from linked homologous or heterologous promoters. However unlike upstream promoter elements, enhancers are active when placed downstream from the transcription initiation site or at considerable distance from the promoter. Many enhancers of cellular genes work exclusively in a particular tissue or cell type (reviewed by Voss et al. 1986, Maniatis et al. 1987). In addition some enhancers become active only under specific conditions that are generated by the presence of an inducer, such as a hormone or metal ion (reviewed by Sassone-Corsi and Borrelli 1986 and Maniatis 1987). Because of these differences in cell specificities of cellular enhancers, the choice of promoter and enhancer elements to be incorporated into a eukaryotic expression vector will be determined by the cell types in which the recombinant gene is to be expressed. Conversely, the use of a prefabricated vector containing a specific promoter and cellular enhancer may severely limit the cell types in which expression can be obtained.

Many enhancer elements derived from viruses have a broader host range and are active in a variety of tissues, although significant quantitative differences are observed among the different cell typees. For example, the SV40 early enhancer is promiscuously active in many cell types derived from a variety of mammalian species, and vectors incorporating this enhancer have consequently been used (Dijkema et al. 1985). Two other enhancer/promoter combinations that are active in a broad range of cells are derived from the long repeat (LTR) of the Rous sarcoma virus genome (Gorman et al 1982b) and from human cytomegalovirus (Boshart et al. 1985).

SUMMARY OF THE INVENTION

The invention relates to a DNA sequence encoding the human IL-18BP promoter (SEQ ID NO: 1), or a fragment such as that in SEQ ID NOS 2 or 3, or a functional derivative thereof wherein the 3' end of said DNA sequence or fragment thereof comprises one or more nucleotides from the 5' end of SEQ ID NO: 5.

More specifically, a derivative according to the invention can be the DNA of the invention mutated at one or more AP1 sites present in a silencer element present in the sequence, and the DNA sequence may further containing a gene operatively linked to the IL-18BP promoter.

In one aspect of the invention, the gene may encode e. g. IL-18BP or a heterologous protein such as luciferase, interferon-beta, TNF, erythropoietin, tissue plasminogen activator, granulocyte colony stimulating factor, manganese-superoxide dismutase, an immunoglobulin, or fragment thereof, growth hormone, FSH, hCG, IL-18, hsLDLR and TNF receptor binding proteins.

The invention provides a vector comprising a DNA sequence sequence encoding the human IL-18BP promoter, a host cell comprising the vector e.g. CHO, WISH, HepG2, Cos, CV-1, HeLA, and Hakat U937 cells, and a method for the production of a recombinant protein comprising culturing the host cell and isolating the recombinant protein produced.

In addition, the invention provides a recombinant virus vector which comprises a portion of the virus genome, a DNA fragment encoding a gene of interest and a DNA fragment comprising a DNA sequence encoding the human IL-18BP promoter. More specifically the virus portion can be e.g. an adeno associated virus, and a retrovirus such as HIV, HFV, MLV, FIV and VSV.

Also the present invention provides a method of regulating cell specific expression of a gene of interest, comprising transducing a target mammalian cell with the virus vector of the invention in a target cell such as an hematopoietic stem cell, and a monocyte. The gene of interest can be e.g. a protein conferring resistance to HIV infection. Regulating cell specific expression of a gene of interest can be used in the treatment of e. g. HIV infection, the treatment of hematopoietic disorders such as SCID, chronic granulomatous disease and thalasemia.

The invention further provides a method of gene therapy for the treatment of a disease in an individual exhibiting elevated IFNγ in a body tissue, comprising the administration of an effective amount of the virus vector of the invention, optionally further comprising administration of IL-6 and/or TNF-a and/or IRF and or C/EBPβ factors.

In another aspect the invention relates to transgenic mice harbouring the DNA sequence encoding a DNA sequence of the invention.

In addition the invention teaches the use of a DNA sequence encoding the human IL-18BP promoter (SEQ ID NO:1), or a fragment or a functional derivative thereof wherein the 3' end of said DNA sequence or fragment thereof comprises one or more nucleotides from the 5' end of SEQ ID NO: 5, in the manufacture of a medicament for the treatment of a disease.

Also, the invention provides a pharmaceutical composition comprising a therapeutically effective amount of a DNA sequence encoding the human IL-18BP promoter (SEQ ID NO:1), or a fragment or a functional derivative thereof wherein the 3' end of said DNA sequence or fragment thereof comprises one or more nucleotides from the 5' end of SEQ ID NO: 5.

DETAILED DESCRIPTION OF THE INVENTION

Figure 1:
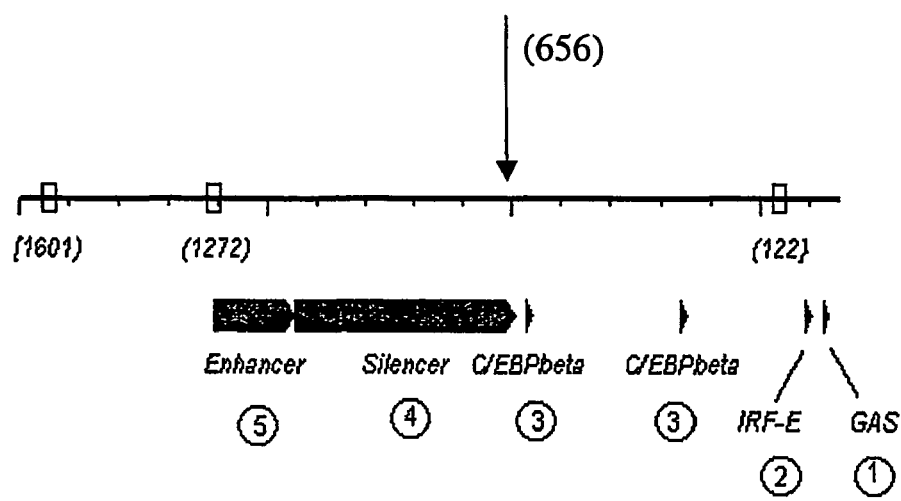
FIG. 1 shows a schematic representation of the promoter region of the IL-18BP gene, including the 5 regulatory elements.

The present invention relates to the promoter of human IL-18BP. This promoter drives the constitutive expression of IL-18BP in particular cells, for example in monocytes and the IFNγ mediated induction of IL-18BP expression in many cells. The promoter of human IL-18BP is capable of directing the constitutive and IFNγ induced expression of a heterologous protein.

The invention relates to a DNA sequence encoding the human IL-18BP promoter (SEQ ID NO:1), or a fragment or a functional derivative thereof wherein the 3' end of said DNA sequence or fragment thereof comprises one or more nucleotides from the 5' end of SEQ ID N: 5.

IL-18BP mRNA is detected in leukocytes, colon, small intestine, prostate and mainly in spleen cells (Novick et al. 1999). In one of the examples below it was shown that IL-18 protein is constitutively expressed in monocytes.

IL-18BP expression was found to be induced by IFNγ, not only in monocytes but also in many different cells and that this induction could be further enhanced by the addition of IL-6 and TNFα.

De novo protein synthesis was found to be essential for IL-18BP gene activation by IFNγ.

The transcription start site of human IL-18BPa mRNA was determined by 5' RACE.

The 3' end mRNA of the Zn finger protein located upstream of the IL-8BP gene was found thereby limiting the potential upstream regulatory sequence of the IL-18BPa to 1601 bases upstream of base 1.

Six regulatory elements (FIG. 1) were identified within this region (from the transcription proximal to the transcription distal): 1- A gamma-activated sequences (GAS) at bases -24 to -32, 2- An IRF-1,2 response element (IRF-E) spanning bases -57 to -69, 3- and 4- two C/EBPβ response elements at bases -309 to -322 and -621 to -634, 5- a scilencer at residues -625 to -1106 and 6- an enhancer element spanning bases -1106 to -1272. A series of luciferase reporter vectors with progressive truncations at the 5'end of the 1601 bp fragment were tested in HepG2 cells (a human hepatocellular carcinoma line). The 1272 kb region set forth in SEQ ID NO: 1 direct both, a basal expression seen in some tissues and cell types, as well as induction by IFNγ. Testing promoter activity on successive truncated DNA fragments within this region demonstrated that a 122 bp DNA fragment, proximal to the transcription start site set forth in SEQ ID NO: 3 comprises the minimal promoter. This minimal promoter is also inducible. However, other regulatory sequences upstream of this minimal promoter did contribute to the extent of induction. A DNA fragment of 635 bp containing in addition to the IRF-1 and GAS elements two C/EBPβ elements, set forth in SEQ ID NO: 2, was found to confer maximal induction of luciferase expression by IFNγ.

In-vivo experiments carried out with IRF-1-deficient mice confirmed the importance of IRF-1 as a mediator of basal as well as IFNγ-induced expression of IL 18BP.

It was found that upon IFNγ induction, the expression of the IRF-1 factor is induced and the factor is complexed to C/EBPβ which is constitutively present in the cells. The complex binds to the proximal GAS promoter element and its adjacent IRF-E promoter element.

The enhancer present at the transcription site distal end was found to interact with the basal promoter through IRF-1.

The present invention relates to the IL18BP promoter of SEQ ID NO:1 or a fragment thereof and methods for regulating gene expression. More particularly, the present invention relates to the isolated DNA sequences of IL-18BP 1272 bp (SEQ ID NO:1) or a fragment thereof such as, 635 bp (SEQ ID NO: 2) and 122 bp (SEQ ID NO: 3) which are capable of directing gene expression.

This IL-18BP promoter region has been cloned and sequenced and corresponds to nucleotides in the 1272 bp upstream of the transcription start site of IL-18BP (SEQ. ID. NO: 1).

The present invention encompasses the entire IL-18BP promoter (SEQ ID NO:1), but also DNA sequences comprising a fragment thereof (SEQ ID NO:2, SEQ ID NO:3), capable of directing gene transcription, and therefore ultimately gene expression, and can be used with other portions of the IL18BP promoter region or alternatively with heterologous promoters or heterologous promoter elements to control gene transcription. This promoter or fragment thereof is capable of induction by IFNγ. Such induction can be further enhanced by overexpression of IRF-1 and/or C/EBPβ and/or by treatment with IL-6 and/or TNFα

Functional derivatives of promoter set forth in SEQ ID NO:1, or fragment thereof such as SEQ ID NO:2 or SEQ ID NO:3 are mutants wherein 1 to 10, preferably 1 to 5, more preferably 1 nucleotide is replaced with another, or is deleted and which are capable of directing gene expression and IFNγ induction.

The DNA sequences of the present invention comprising a IL-18BP promoter (SEQ ID NO: 1) or a fragment thereof such as that in SEQ ID NO:2 or SEQ ID NO:3, can be isolated using various methods known in the art. At least three alternative principal methods may be employed:

(1) the isolation of the DNA sequence from genomic DNA which contains the sequence; (2) the chemical synthesis of the DNA sequence; and (3) the synthesis of the DNA sequence by polymerase chain reaction (PCR).

In the first approach, a human genomic DNA library can be screened in order to identify a DNA sequence comprising a IL-18BP promoter or IL-18BP promoter element.

In the second approach, a DNA sequence comprising a IL-18BP promoter or a IL-18BP promoter element can be chemically synthesized. For example, a DNA sequence comprising a IL-18BP promoter region or a IL-18BP promoter can be synthesized as a series of 100 base oligonucleotides that can then be sequentially ligated (via appropriate terminal restriction sites) so as to form the correct linear sequence of nucleotides.

In the third approach, a DNA sequence comprising a IL-18BP promoter region or a IL-18BP promoter can be synthesized using PCR. Briefly, pairs of synthetic DNA oligonucleotides at least 15 bases in length (PCR primers) that hybridize to opposite strands of the target DNA sequence can be used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, U.S. Pat. Nos. 4,683,195 and 4,683,202.

The IL-18 BP promoter of the invention was shown to be capable of conferring basal expression and also induced expression by IFNγ of an heterologous gene. Thus, the promoter of IL-18BP have both basal and inducible activity.

While the nucleotide sequence of the promoter is set forth in SEQ. ID. NO.1 or to fragments thereof having promoter activities and reference is made to such sequence in the specification, it is recognized that nucleotide derivatives can be made which do not affect the promoter or promoter element function. These modified nucleotide sequences may be prepared, for example, by mutating the nucleotide sequence so that the mutation results in the deletion, substitution insertion, inversion or addition of one or more nucleotides using various methods known in the art. For example, the methods of site-directed mutagenesis described in Taylor, J. W. et al., Nucl. Acids Res. 13, 8749-8764 (1985) and Kunkel, J. A., Proc. Natl. Acad. Sci. USA 82, 482-492 (1985) may be employed. In addition, kits for site-directed mutagenesis may be purchased from commercial vendors. For example, a kit for performing site-directed mutagenesis may be purchased from Amersham Corp. (Arlington Heights, Ill.). The present invention encompasses DNA containing sequences at least 50% identical and preferably 75% identical and more preferably 90% identical to SEQ ID NO:1, SEQ ID NO:2 and SEQ ID NO:3 respectively, provided that the promoter activity is retained and/or enhanced. One such derivative e.g. in SEQ ID NO:1 is that mutated in one or all of the three AP1 sites present in the silencer region.

The nucleotide sequence comprising the promoter of IL-18BP, a fragment thereof and/or a derivative thereof can be operably linked to the coding region of any gene of interest to express that gene in an appropriate host cell. By operably linked is intended operably linked for promoter and elements. For expression of a gene of interest, it is preferred that the entire IL-18BP promoter in SEQ. ID. NO.1: or a fragment thereof such in SEQ ID 2 or SEQ ID NO:3 or a derivative thereof is operably linked to the gene of interest. As shown below in the example section, the IL-18BP promoter, or a fragment thereof such as that in SEQ ID NO:2 or in SEQ ID NO:3 is capable of directing the expression of heterologous genes. The expression of homologous genes with the promoter of the invention is also contemplated.

The promoter may further contain an intron, for example the first intron of IL-18BP.

An "operably linked" IL-18BP promoter or promoter element will direct the transcription of a nucleic acid molecule joined in proper reading frame. With regard to heterologous promoters, the promoters and elements of the invention are operably linked when they control the function of such heterologous promoters.

As noted above, the IL-18BP promoter, a fragment thereof and a derivative sequences thereof of the present invention can be utilized to express any gene of interest. Typically, an expression vector is used for this purpose. Thus, the present invention further concerns expression vectors comprising an isolated DNA sequence capable of directing gene expression which comprises a IL-18BP promoter or a fragment thereof or a derivative thereof. The expression vectors preferably contain an IL-18BP promoter a fragment thereof or derivative thereof having a nucleotide sequence corresponding to SEQ ID NO:1, SEQ ID NO:2 or SEQ ID NO:3, respectively or fragments thereof and/or derivatives. Also preferred are expression vectors further comprising a homologous or heterologous gene operatively linked to the IL-18BP promoter or a fragment thereof and/or a derivative thereof modified nucleotide sequence thereof.

Expression vectors of utility in the present invention are often in the form of "plasmids", which refer to circular double stranded DNAs which, in their vector form, are not bound to the chromosome. However, the invention is intended to include such other forms of expression vectors which serve equivalent functions and which become known in the art subsequently hereto.

Expression vectors useful in the present invention typically contain an origin of replication, a IL-18BP promoter located in front of (i.e., upstream of) the gene of interest, transcription termination sequences and the remaining vector. The expression vectors can also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases. The characteristics of the actual expression vector used must be compatible with the host cell which is to be employed. An expression vector as contemplated by the present invention is at least capable of directing the transcription, and preferably the expression, of the gene of interest dictated by the IL-18BP promoter region or IL-18BP promoter or a modified nucleotide sequence thereof. Suitable origins of replication include, for example, that of the Simian virus 40 (SV40). Suitable termination sequences include, for example, that of the Simian virus 40 (SV40). The promoter of the invention can be employed for the expression of virtually any gene of interest, for example, those encoding therapeutic products such as interferon-beta, TNF, erythropoietin, tissue plasminogen activator, granulocyte colony stimulating factor, manganese-superoxide dismutase, an immunoglobulin, or fragment thereof, growth hormone, hsLDLR, FSH, hCG, IL-18, TNF receptor binding proteins and IL-18 binding proteins. All of these materials are known in the art and many are commercially available.

Suitable expression vectors containing the desired coding and control sequences may be constructed using standard recombinant DNA techniques known in the art, many of which are described in Sambrook, et al., Molecular Cloning: A Laboratory Manual, 2nd edition, Cold Spring Harbor Laboratory, Cold Spring Harbor, N.Y. (1989).

The present invention additionally concerns host cells containing an expression vector comprising an isolated DNA sequence capable of directing gene expression which comprises a IL-18BP promoter region or a IL-18BP promoter or modified nucleotide sequences thereof. Preferably, the IL-18BP promoter region has the nucleotide sequence corresponding to 1272 bp upstream of the transcription start site of IL-18BP set forth in SEQ D) NO:1, or a fragment thereof such as the nucleotide sequence corresponding to 635 bp upstream of the transcription start site set forth in SEQ ID NO: 2 or a fragment thereof such as the nucleotide sequence of 122 bp upstream of the transcription start site set forth in SEQ ID NO:3. Also preferred are host cells containing an expression vector further comprising a homologous or heterologous gene operatively linked to the IL-18BP promoter region or the IL-18BP set forth in SEQ ID NO:1 or a fragment thereof. Suitable host cells include, for example, human HeLa cells or African Green Monkey cells CV-1 and COS-1, CHO cells, HepG2, WISH cells, Hakat U937 etc.

Preferred are host cells containing receptors for IFNγ, which allow induction of the IL-18BP promoter and therefore enhanced expression of the gene of interest.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection and viral or phage infection can also be employed.

Once an expression vector has been introduced into an appropriate host cell, the host cell can be cultured and the polypeptide encoded by the gene of interest can be isolated. Alternatively once an expression vector has ben introduced into in an appropriated host cell, the cell can be cultured and after reaching a desired cell density, the cells can be stimulated with IFNγ and the polypeptide encoded by the gene of interest can be isolated.

Host cells containing an expression vector which contains a DNA sequence coding for a gene of interest may be identified using various methods known in the art. For example, DNA-DNA hybridization, assessing the presence or absence of marker gene functions, assessing the level of transcription as measured by the production of mRNA transcripts of the gene of interest in the host cell, and detecting the gene product immunologically can be employed.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463-5467 (1977), or the Maxam-Gilbert method as described in Proc. Natl. Acad. Sci. USA 74, 560-564 (1977) may be employed.

It should be understood specific nucleotides or regions within the IL-18BP promoter may be identified as necessary for regulation. These regions or nucleotides may be located by fine structural dissection of the elements, and can be studied by experiments which analyze the functional capacity of promoter mutants. For example, single base pair mutations of promoter elements or progressive deletions, as such employed in the example section below, can be generated utilizing PCR. In this fashion, a number of mutated promoter regions or deletion constructs are amplified, and then cloned back into reporter constructs and evaluated with transfection and luciferace assay techniques (as set forth in the example section below). These amplified fragments can be cloned back into the context of the IL-18BP promoter and also into the heterologous promoter constructs. In this fashion, the exact nucleotide sequences that are important in directing gene transcription are identified.

This analysis will also identify nucleotide changes which do not effect promoter function, or which may increase promoter function. Thus, functional derivative promoters and promoter elements can also be constructed.

Functional analysis of the promoter region or promoter can be facilitated by footprint and gel-shift studies. Knowledge of the exact base pairs important in mediating binding of proteins provides evidence of bases important in mediating the transcriptional response.

The invention therefore further encompasses the base pairs important in DNA-protein interaction. Such base pairs can be elucidated. Genomic fragments containing the areas of interest can be employed in in vitro footprinting experiments [Galas et al., Nucleic Acids Res. 9, 6505-6525 (1981)]. Isolated restriction fragment can be radiolabled and subsequently incubated with nuclear extracts made with established techniques from cells expected to contain DNA binding proteins which will bind to the fragment [for example, Dignam et al., Nucleic Acids Res. 11, 1475-1489 (1983)]. Labeled DNA fragments are incubated with the nuclear extracts, digested with DNAse I, and electrophoresed on a denaturing polyacrylamide gel. DNA binding proteins in the cell extract bind to their recognition sequence contained in the labeled restriction fragment, and protect the DNA from digestion by the DNAse. Regions of protection delineate the binding site. Maxam and Gilbert sequencing reactions of the fragment can be used as a marker to define the nucleotides protected from DNAse digestion.

The invention is further drawn to the identification and characterization of trans-acting factors which interact with the promoter or promoter elements. Cis-acting regulatory sequences serve as binding sites for proteins which are termed transacting factors (TAF) [Dynan W. S., Tjian T. Nature 316, 774-778 (1985); Maniatis, T. et al., Science 236, 1237-1245 (1987)]. Each gene is presumed to bind one or more proteins at each of its regulatory sequences, and these proteins interact with one another and RNA polymerase II in a fashion that controls transcription.

TAFs have been identified in nuclear extracts by their ability to bind to and retard electrophoretic mobility of cis-acting sequence DNA fragments [Dignam, J. D. et al., Nucleic Acids Res. 11, 1475-1489 (1983); Dynan, W., Cell 58, 1-4 (1989); Fletcher, C. et al., Cell 773-781 (1987); Scheidereit, C. et al., Cell 51, 783-793 (1987)].

The cis-acting sequences are useful in gel retardation assays to determine binding activity in nuclear extracts. The technology for gel shift assays is described in the literature and includes many of the same reagents used in footprint experiments [Fried, M. et al., Nucleic Acids Res. 9, 6505-6525 (1981); Revzin, A., Biotechniques 7, 346-355 (1989); Strauss, F. A. et al., Cell 37, 889-901 (1984)]. Either 32 P-labeled restriction fragments or annealed pairs of complementary oligos are incubated with nuclear extracts and poly d(I-C) in a binding buffer, and the products of this reaction electrophoresed on a non-denaturing polyacrylamide gel. The location of the DNA fragment on the gel as determined with autoradiography is retarded in cases where protein has bound to the DNA. The extend of the retardation is a relative function of the size of the protein.

The binding proteins so identified can then be purified and ultimately cloned using known techniques.

The promoter of IL-18BP also find use in transgenic studies. Transgenic mice provide a powerful genetic model for the study of a number of human diseases including cancer. They have also provided an important in vivo method for studies of gene regulation that have confirmed and extended observations made with transfection reporter gene (e.g. luciferase)

experiments [Palmiter, F. L. et al., Ann. Rev. Genet. 20, 465-499 (1986)]. Studies aimed at dissecting the signals allowing developmental relation of gene expression can rarely be performed in cell culture models and is probably best studied with a transgenic model. This type of experiment is possible because of the remarkable conservation between species of regulatory sequences, such that human regulatory signals are accurately interpreted by the mouse transcription machinery.

Constructs expressed in transgenic mice could therefore provide much information about the regulation of the IL-18BP gene.

Transgenic mice can be made by methods known in the art. The most widely used method through which transgenic animals have been produced involve injecting a DNA molecule into the male pronucleus of a fertilized egg [Brinster et al., Cell 27, 223 (1981); Costantini et al., Nature 294, 982 (1981); Harpers et al., Nature 293, 540 (1981); Wagner et al., Proc. Natl. Acad. Sci. USA 78, 5016 (1981); Gordon et al., Proc. Natl. Acad. Sci. USA 73, 1260 (1976)].

Once the DNA molecule has been injected into the fertilized egg cell, the cell is implanted into the uterus of recipient female and allowed to develop into an animal. Thus, all of the cells of the resulting animal should contain the introduced gene sequence.

The resulting transgenic mice or founders can be bred and the offspring analyzed to establish lines from the founders that express the transgene. In the transgenic animals, multiple tissues can be screened to observe for gene expression. RNA studies in the various mouse lines will allow evaluation of independence of the integration site to expression levels of the transgene. See, Hogan, B. et al., Manipulating the mouse embryo: a laboratory manual, Cold Spring Harbor Press, Cold Spring Harbor, N.Y. (1986).

The IL-18BP promoter and promoter elements may also provide a useful means for carrying out gene therapy.

"Gene therapy" is the administration of genetic material to modify or manipulate the expression of a gene product to alter biological properties of living cells for therapeutic use.

The cells can be allogeneic or autologous. Cells may be modified ex-vivo for subsequent administration to the subject or altered in vivo by gene therapy products given directly to the subject.

For the most part, constructs comprising the IL-18BP promoter or fragment thereof and/or a derivative thereof will be utilized to target gene expression in those cells when the IL18BP gene is normally expressed, for example mononuclear cells. Any means available in the art for transfer of the constructs into animals, including humans, can be utilized. This includes viral vectors, particularly retroviral vectors (see, for example, Zweibel et al, Science 243, 220 (1989), and the references cited therein), as well as other methods.

Recombinant AAV vectors have been shown quite promising for therapeutic gene delivery in liver and skeletal muscle (Snyder et al. 1997, Murphy et al. 1997, Song et al. 1998, Snyder et al. 1999, Herzog et al. 1997). Mice generated by disrupting the clotting factor IX gene exhibit severe bleeding disorder and closely resemble the phenotype seen in hemophilia B patients. It has been reported (Wang et al. 1999) that a single intraportal injection of a recombinant adeno-associated virus (AAV) vector encoding canine factor IX cDNA under the control of a liver-specific enhancer/promoter leads to a long-term and complete correction of the bleeding disorder.

Retroviral vectors, derived from oncoretrovirus such as the murine leukemia virus (MVL), have been the most widely used vectors for gene transfer because the vector genome integrates into the chromosomes of target cells, resulting in stable expression of transgenes (I. M. Verma and N. Somnia. Nature 389, 239 (1997) however these vectors were proven to be good especially for dividing cells. Letiviruese vectors such as HIV vectors are being currently used for nondividing cells Mioshi et al. Science 1999 283: 682-686. The ability of lentiviruses to infect nondividing cells such as macrophages makes them good candidates for use as gene transfer tools. HIV vectors facilitate transduction of quiescent human hematopoietic stem cells (HSCs).

Human hematopoietic stem cells (HSC) are an attractive target for gene therapy of inherited hematopoietic disorders as well as other acquired disorders because these cells have the ability to regenerate the entire hematopoietic system. For example hematopoietic stem cells can regenerate monocytic cells which are known to be involved in human immunodeficiency virus-1 (HIV-1) pathogenesis.

Despite more than 15 years of research in the field of gene therapy using hematopoietic stem cells, the major hurdle remains the inability to efficiently and stably insert genes into these cells. Retroviral vectors based upon the Moloney murine leukemia virus (MLV) have been used most extensively, but yield relatively low gene transfer into pluripotent human HSC and gene expression which is often unsatisfactory.

Recently, attempts of genetic modification of hematopoietic stem cells with genes that inhibit replication of HIV-1 are aimed, for the development of monocytes resistant to HIV-1 infection (Kohn et al. 1999).

Theoretically, insertion of a gene capable of conferring resistance to HIV-1 into hematopoietic stem cells would result in that gene being present in the descendant mature monocytes and other HIV-1 susceptible cells Thus, the use of a promoter which is active in monocyte cells such as the promoter of IL-18BP or a fragment thereof, for HIV-1 gene therapy is advantageous.

Gene therapy of most blood genetic disorders (e.g. SCID chronic granulomatous disease, thalassemia etc.) requires ex vivo gene transfer into transplantable, self renewing HSCs and regulation of transgene expression in one or more cell lineages. Correction of disorders affecting a specific progeny of HSCs (e.g. hemoglobinopathies or thalassemias, HIV-Infection) requires restricting expression of therapeutic gene in cell lineage specific fashion (Iotti et al. 2002). In these cases, transcriptional targeting of the transferred gene is mandatory. Gene expression in different cell types is dependent on the relative strength of the promoter used. However, most preclinical studies carried out so far have relied on the use of viral, constitutive promoters to drive transgene expression. For example in HIV-1 vector uses an internal CMV promoter and the murine CMV promoter the murine retroviral vector LTR. Appropriate transgene regulation in the framework of a retroviral vector is a difficult task, due to transcriptional interference between the viral long terminal repeat (LTR) and internal enhancer-promoters and genetical instability of complex regulatory sequences. In the present invention the promoter of IL-18BP which is known to drive transcription in mononuclear cells is used to drive transgene expression in HSCs, the precursor of such mononuclear cells.

Genetic modification of hematopoietic stem cells with "anti HIV genes" could lead to development of lymphocytes and monocytes resistant to HIV infection after transplantation. HSC of HIV-1 infected patients can be recovered, CD34+ cells isolated, transduced in vitro with a retroviral vector carring an HIV-1 inhibitory protein under the control of the IL-18BP promoter (instead of the retroviral promoter) and reinfusing these cells into these patients (Kohn et al. 1999).

The most commonly used source of HSC is peripheral blood hematopoietic stem cells (PBSC), which have largely replaced bone marrow in the setting of autologous transplantation (Gale et al. 1992 and Kessinger et al. 1991). PBSC are mobilized from the bone marrow into the peripheral circulation by administration of factors such as G-CSF or GM-CSF for 3-5 days and can then be collected by leukapheresis. Several studies have shown that engraftment occurs faster when transplanting peripheral blood stem cells instead of bone marrow (Henon et al 1992 and Chao et al. 1993). The clonogenic progenitor cells contained in G-CSF-mobilized PBSC are quite susceptible to retroviral-mediated gene transfer, whereas the transduction rate of long-term reconstituting stem cells in PBSC is no better than bone marrow (Breni et al. 1992, Cassel et al. 1993, Dunbar et al. 1995). It has been shown that HIV-1 infected subjects can have successful mobilization and collection of G-CSF-mobilized PBSC without any increase in endogenous HIV-1 levels, at least during early stages of disease (Junker et al. 1997 and Slobod et al. 1996).

Another source of hematopoietic stem cells is umbilical cord blood (UCB) which has been shown to be susceptible to retroviral transduction, potentially even more so than bone marrow cells (Moritz et al. 1993 and Hao et al. 1995). Use of UCB cells HSC could be particularly beneficial for HIV-1 infected neonates. Since transmission is mostly perinatal, the umbilical cord blood should contain normal numbers and function of hematopoietic stem cells, which may be diminished in the bone marrow of HIV-1 infected children and adults (Kearns et al. 1997).

A large number of synthetic genes have been developed which can suppress HIV-1 replication ("anti-HIV-1 genes"), including: antisense, ribozymes, dominant-negative mutants (e.g. RevM10), RNA decoys, intracellular antibodies to prevent expression of viral proteins or cellular co-receptors, etc. (Veres et al. 1996, Zhou et al. 1994, Couture et al 1996, Malim et al. 1989, bahner et al 1993 and Sullenger et al. 1990, Lee et al. 1994, Marasco et al 1997 and Chen et al. 1997). In many cases, these anti-HIV-1 genes have been shown in model systems to be able to significantly suppress the replication of HIV-1 and in some cases even limit virus entry into cells (36, 39-44). If essentially 100% of a patient's HSC and the resultant monocytic cells could be made incapable of supporting HIV-1 replication, it is likely that decreased viral burdens would result. Theoretically, active inhibition of HIV-1 replication in 99.9% of the susceptible cells would be required to produce a 3-log reduction in virus load, an effect often produced by highly-effective anti-retroviral therapy. However, with the limited capabilities to effectively transduce high percentages of human hematopoietic stem cells, it is not currently possible to protect the majority of susceptible cells. An alternative mechanism for efficacy is based on the possibility that cells engineered to be incapable of supporting active HIV-1 replication may be protected from viral-induced cytopathicity and thus have a selective survival advantage compared to non-protected cells. In that case, a modest number of protected cells may comprise an increased percentage of all monocytes, leading to some preservation of immune function.

The present invention also relates to pharmaceutical compositions comprising a pharmaceutically acceptable carrier and a virus comprising a sequence of the present invention corresponding to the IL-18BP promoter region or promoter operably linked to a gene of interest encoding for a suitable drug. These compositions may be used preferably for targeting a drug to tissues in which the levels of IFNγ are elevated.

Having now described the invention, it will be more readily understood by reference to the following examples that are provided by way of illustration and are not intended to be limiting of the present invention.

EXAMPLES

Example 1

Basal Expression of IL-18BP in Monocytes.

IL-18BP MrRNA is detected in leukocytes, colon, small intestine, prostate and particularly in spleen cells (Novick et al. 1999). Spleen cells consist of macrophages, lymphocytes, and plasma cells with additional cells derived from the circulation.

In order to determine expression of IL-18BP protein in cells, a specific ELISA test was used (Example 12). Human peripheral blood mononuclear cells (PBMC) were found to constitutively produce IL18BP (0.7-1.5 ng/ml). U-937 cells, a cell line derived from malignant cells obtained from the pleural effusion of a patient with histiocytic lymphoma, did not express any IL-18BP. U-937 cells can be induced to terminal monocytic differentiation by treatment with phorbol esters. A basal IL-18BP expression of 0.07±0.01 ng/ml was detected only after differentiation of the cells into macrophage-like cells by stimulation with TPA (10 ng/ml). These results show that IL-18BP is constitutively produced in monocytes and macrophages.

Example 2

Induction of IL-18BP Expression in Various Different Cells.

Figure 2:
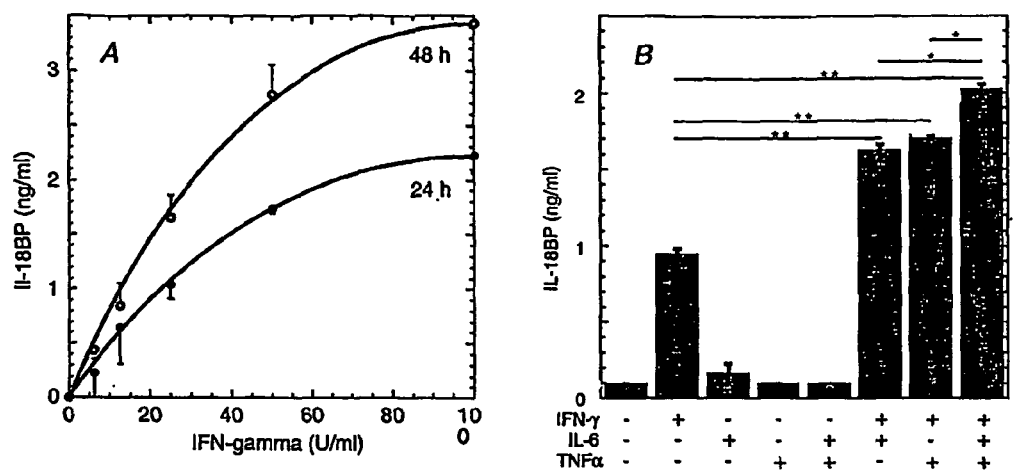
FIG. 2 shows the Kinetics of IL-18BP induction and synergy with TNFα and IL-6. (A) IFNγ induces IL-18BP in a dose and time-dependent manner in human WISH cells. Cells were incubated with the indicated concentrations of IFNγ for 24 and 48 h. (B) Synergistic effects of TNFα IL-6 and their combination on IFNγ-induced IL-18BP. HepG2 cells were incubated with the indicated combinations of IFNγ (100 U/ml), TNFα. (20 ng/ml) and IL-6 (300 U/ml). Induction of IL-18BP by each combination was significantly higher (p<0.05) then induction by IFNγ alone. Data are mean SD (n=3, for A. n=4, for B).

It has been previously reported that IFNγ induced IL-18BP mRNA and protein in various cell lines such as a keratinocyte cell line, a colon carcinoma cell line and in primary renal mesangial cells (Muhl et al. 2000). The induction of IL-18BP in various human cell lines and in peripheral blood mononuclear cells (PBMC) by IFNγ and other cytokines was studied. IFNγ induced IL-18BP expression (see Example 11 for monitoring mRNA and Example 12 for ELISA) in a dose-dependent manner, exhibiting an $EC_{50}$ at 50 U/ml in WISH and HepG2 cells (FIG. 2 A and B). IL-18BP apparently accumulated in the culture supernatants of WISH cells, as its concentration was higher at 48 h compared with 24 h (FIG. 2 A).

Human peripheral blood mononuclear cells (PBMC) constitutively produced IL-18BP (0.7-1.5 ng/ml), and treatment with IFNγ (100 U/ml) increased the level of IL-18BP by 1.7±0.1 and 2.1±0.3 fold at 24 and 48 h, respectively (p<0.05, n=4). No effect on IL-18BP production was seen upon pretreatment of the PBMC with TPA.

IL-18BP induction by IFNγ was tested in the U937 cell line. IFNγ did not induce IL-18BP in undifferentiated U937 cells, however, following differentiation with phorbol ester (TPA, 10 ng/ml) into macrophage-like cells, a basal level of IL-18BP (0.07±0.01 ng/ml) was obtained, and increased by 4.6±0.05 fold upon induction with IFNγ(100 U/ml, 24 h), further increasing at 96 h (not shown).

The effect of other cytokines, such as IFNα2, IFNβ, IL-1, IL-6, IL-12, IL-18 and TNFα, on IL-18BP expression was tested in HepG2 cells (FIG. 2B). The results obtained following incubation of the cells with the different cytokines in the presence or the absence of IFNγ (FIG. 1 PNAS web) show that IFNα2, IFNβ, IL-1, IL-6, IL-12, IL-18 and TNFα did not induce IL-18BP alone. However, in HepG2 cells IL-6 and TNFα acted synergistically with IFNγ, providing a statistically significant increase of IL-18BP.

These results indicate that IL-18BP can be induced by IFNγ, in monocytes and in many different cells. Induction of IL-18BP by IFNγ is further enhanced by the addition of IL-6 and TNFα.

Example 3

The IL-18BP Gene is Transcriptionally Regulated by IFNγ, Requiring De Novo Protein Synthesis.

Figure 3:
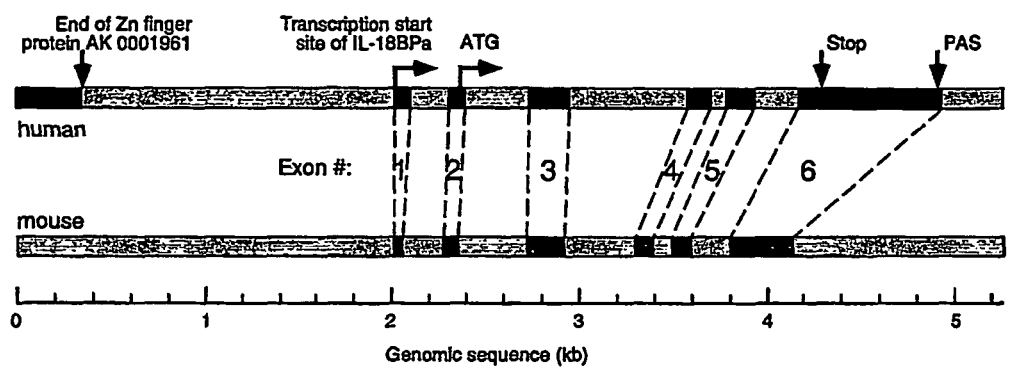
FIG. 3. shows a schematic representation of the conserved exon-intron organization of the human and mouse IL-18BP genes. The human IL-18BPa gene was compared with the mouse IL-18BPd gene. Exons are indicated. Transcription start site, translation start site (ATG), stop codon (Stop) and the polyadenylation signal (PAS) are indicated for the human IL-18BPa gene.

In order to check whether the induction of IL-18BP mRNA by IFNγ is at the transcriptional level, the effect of interferon on HepG2 and Wish cells was measured in the presence of a translation inhibitor, Actinomycin D (FIG. 3A). Increase in IL-18BP mRNA levels were detectable by semi-quantitative RT-PCR after 3 h of treatment with IFNγ in HepG2 cells and only after 5 h in Hakat and WISH cells. Pre-treatment of HepG2 and WISH cells with Actinomycin D prior to IFNγ stimulation abolished the expression of IL-18BP mRNA at various time points, indicating that IFNγ stimulates de-novo mRNA synthesis.

Accumulation of IL-18BP was apparent 24 h and later following IFNγ treatment, supporting a dependence of IL-18BP expression on preceding induction of proteins, e.g. transcription factors, by IFNγ. Therefore in order to confirm such hypothesis, a protein inhibitor, cycloheximide, was further employed to test whether induction of IL-18BP mRNA by IFNγ requires de-novo synthesis of proteins. The results summarized in FIG. 3B show that pre-treatment of the cells with cycloheximide abolished the induction of IL-18BP mRNA. This result indicates that de novo protein synthesis is essential for IL-18BP gene activation by IFNγ.

Example 4

Defining the Transcription Start Site of IL-18BPa and its Promoter Region, in Order to Map the IL-18BP Promoter.

In order to study the IL-18BP promoter region, it is required first to specifically locate the transcription start site.

Figure 4:
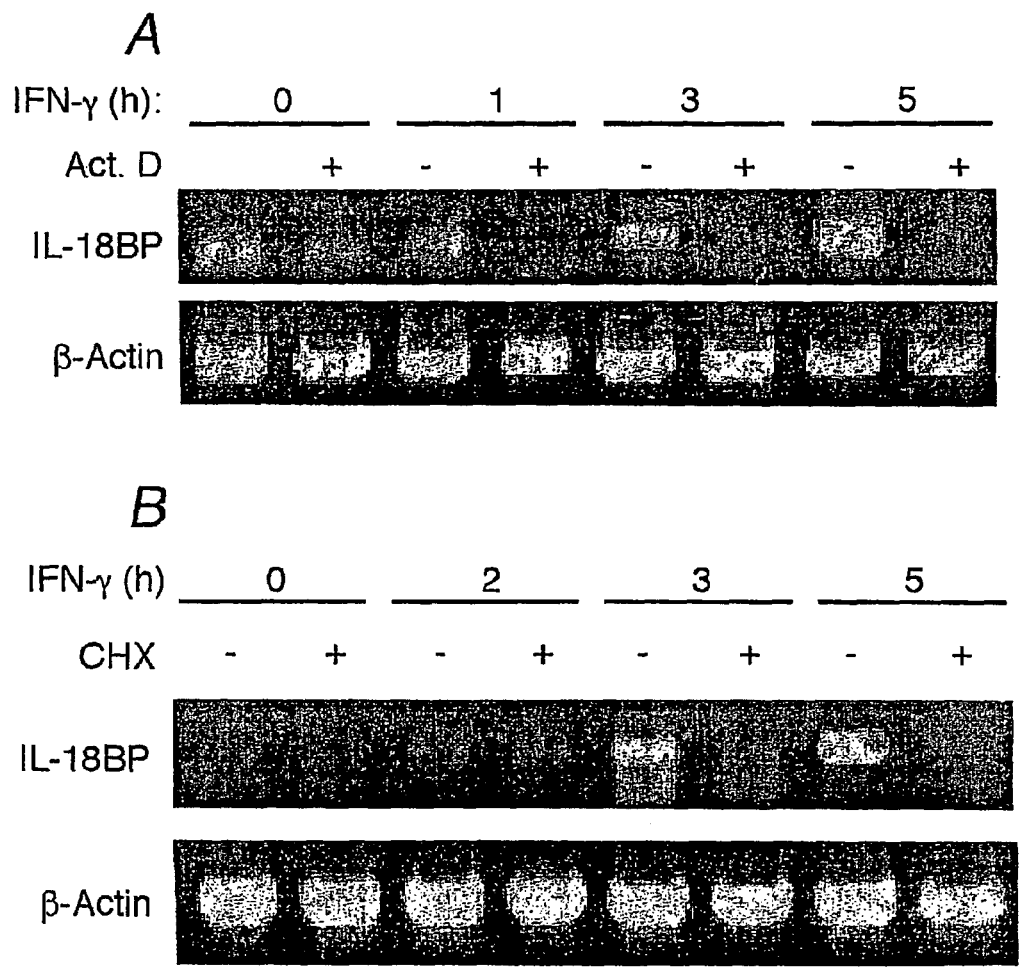
FIG. 4 shows that the induction of IL-18BP by IFNγ is at the transcriptional level and depends on de novo protein synthesis. (A) semi-quantitative RT-PCR of IL-18BP mRNA from HepG2 cells that were pre-incubated with actinomycin D (1 μg/ml, 30 min), washed and incubated with IFNγ (100 U/ml) for the indicated times. RT-PCR of β actin mRNA is shown as a control (B) semi-quantitative RT-PCR of IL-18BP mRNA from HepG2 cells that were pre-incubated with cycloheximide (20 μg/ml) and IFNγ (100 U/ml) for the indicated times.

The transcription start site of human IL-18BPa mRNA was determined by 5' RACE (RACE Example 14). Only one PCR product, corresponding to IL-18BPa, the most abundant splice variant, was obtained by 5' RACE. DNA sequence analysis of this product revealed the transcription start site and an additional exon of 50 bp following the transcription start site at the 5'-end of human IL-18BPa mRNA, corresponding to positions 785-835 of the genomic IL-18BP DNA (can be found in the Entrez pubmed nucleotide database, accession No. AF110798). Accordingly, a new exon-intron map was generated by comparing the genomic DNA with the mRNA to which the new 5' exon was added. (See FIG. 4).

Having the transcription start site of IL-18BPa (base 1), the human genomic DNA upstream of base 1 (chromosome 11q clone:RP11-757C15, Accession No AP000719.4 nucleotides upstream of base 152,178) corresponding to the IL-18BP promoter region could be further analysed. Comparison of this DNA to the expressed sequence tag (EST) database at NCBI by the BLAST program revealed an upstream gene at the +strand, coding for a Zinc-finger protein (Accession No. AK001961). The deposited mRNA sequence of this Zn finger protein was further elongated by the "Instant RACE" program (www.LabOnWeb.com), which scanned an extensive collection of human ESTs. The program placed the 3' end mRNA of the Zn finger protein at nucleotide 150,517 of the genomic clone RP11-757C15, thereby limiting the potential upstream regulatory sequence of the IL-18BPa to 1661 bases upstream of base 1.

Example 5

Exploring the Minimal Promoter, Upstream of the IL-18BP Gene, Capable for Promoting Constitutive Expression of a Heterologous Gene.

In order to find the minimal DNA fragment, upstream of the IL-18BP gene, capable of directing expression of an hexogenous gene such as the luciferase reporter gene, a vector containing up to 1601 bp corresponding to the DNA sequence upstream of base 1 and including 50 bp downstream of the transcription strat site (SEQ ID NO: 5) and vectors having truncated forms of this DNA (FIG. 5A) fused to the luciferase gene were generated (Example 15). Luciferase activity in human HepG2 cells (a human hepatocellular carcinoma line) transfected with a vector (pGL3(1601)) comprising the 1601 bp upstream DNA was 10.3±0.9 fold higher than that obtained with the empty pGL3 vector. Such activity was not observed when the same DNA was inserted in the opposite orientation (pGL3(-1601). This result demonstrated that the 1601 bp DNA upstream of base 1 has basal promoter activity. Sequence examination of this 1601 bp DNA fragment revealed that it does not include a TATA box element, but had several GC-rich domains near the transcription start site at bases -3 to -9, -39 to 48 and -122 to -132. Analysis of the 1601 bp DNA sequence by the program TFSEARCH identified a gamma-activated sequence (GAS) at bases -24 to -32 (FIG. 1). Further analysis revealed an IRF1,2 response element (IRF-E) spanning bases -57 to -69 and two C/EBPβ response elements (C/EBP-E) at bases -309 to -322 and -621 to -634.

A series of luciferase reporter vectors with progressive truncations at the 5' end of the 1601 bp fragment were tested. The results summarized in FIG. 5A show that all constructs, including pGL3 (122), containing only the IRF and GAS elements, were at least as effective as pGL3(1601) in supporting basal promoter activity.

Figure 5:
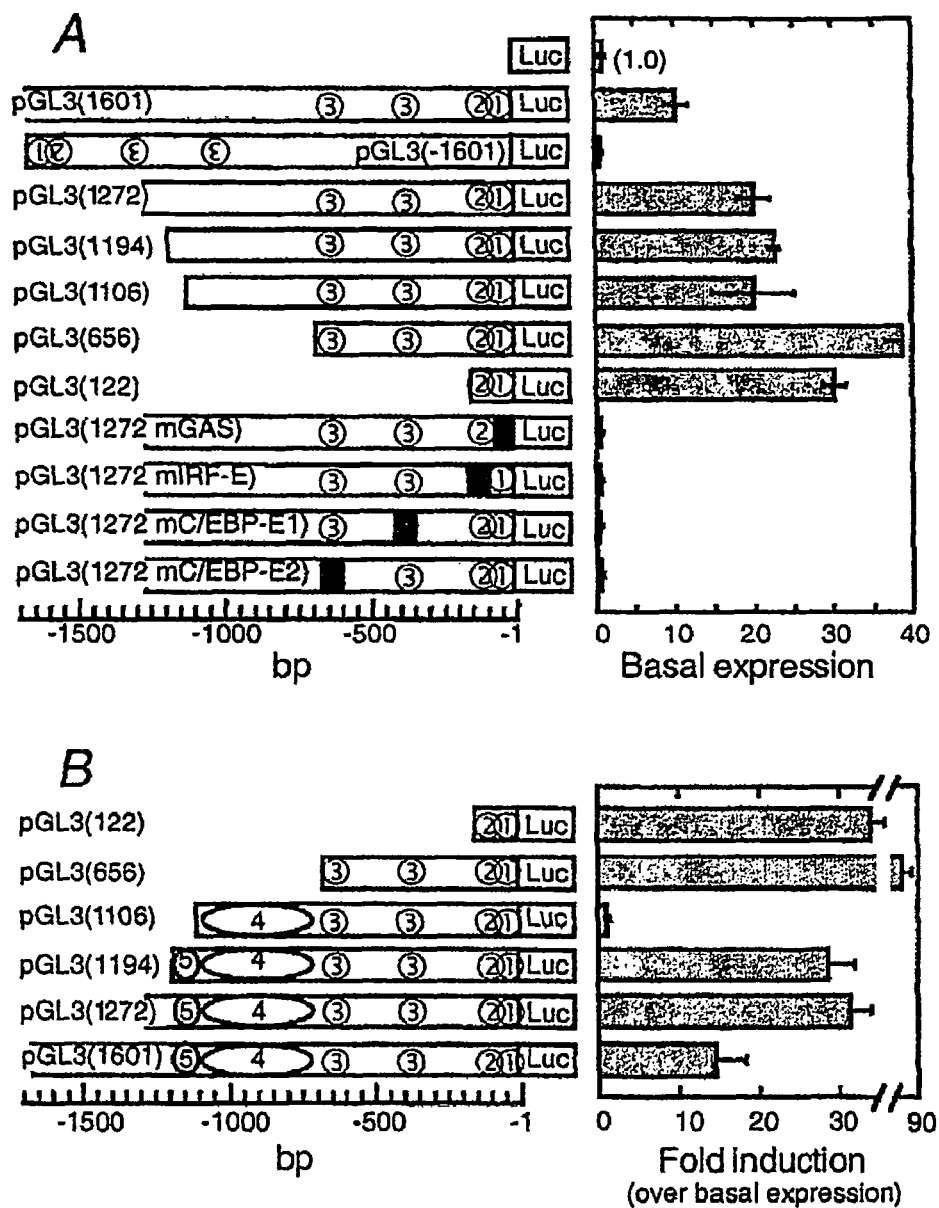
FIG. 5 shows the basal and IFNγ-induced activity of luciferase reporter vectors carrying the human IL-18BP promoter. Insert size, extending from the transcription start site (+1) is given in parentheses. Circled numbers represent the various response elements: 1. GAS. 2. IRF-E. 3. C/EBP-E (2 sites). Scilencer 5. Distal enhancer. Filled squares depict mutation in a specific response element. HepG2 cells were co-transfected with the indicated reporter vector and pSV40 βGAL. All luciferase values were normalized to βgalactosidase activity. (A) luciferase activity in extracts of un-induced cells relative to that of cells transfected with pGL3—Basic vector. (B) luciferase activity in cells transfected with selected vectors and induced with IFNγ. Fold induction is over basal activity as given in (A).

These results revealed that the 122 bp fragment (SEQ ID NO:3) comprising the IRF and GAS elements are sufficient for promoting basal activity of an heterologous gene (FIG. 5A).

Example 6

Exploring the Minimal Promoter, Upstream of the IL-18BP Gene, Capable for Promoting Inducible Expression of a Heterologous Gene.

In order to identify the minimal DNA fragment, upstream region of the IL-18BP promoter, capable of promoting IFNγ induced luciferace expression, the truncated DNA vectors from the preceding example were tested in transfected HepG2 cells in the presence of IFNγ (FIG. 5B for transfections see example 16).

The results summarized in FIG. 5B show that after 24 h IFNγ increased the luciferase activity by 33 fold over the basal expression level in the vector including only IRF-E and GAS elements (pGL3(122) vector). This result demonstrates that the IRF-E-GAS pair alone can mediate heterologous gene induction by IFNγ. Inclusion of C/EBP-E1 and 2 elements (pGL3(656)) significantly increased the induction of luciferase activity by IFN-γ to 88 fold over the basal activity, demonstrating the importance of these elements in inductivity by IFNγ. In contrast, inclusion of an additional upstream DNA to such insert (pGL3(1106)) abolished the induction of luciferase activity above its basal level. This result suggested that a silencer element resides within bases -656 to -1106 (Upstream of the second C/EBP-E1 element). It was demonstrated that three AP1 response elements are present within the silencer region and that c-Jun binds to, and is involved in silencing of the IL-18BP gene through all of such three AP-1 response elements.

Further extension of the promoter by 88 bases upstream the silencer (pGL3(1272)) restored the response to IFNγ, suggesting that an enhancer element resides in bases -1106 to -1272, and its activation by IFNγ suppresses the effect of the neighboring silencer. Further extension of the sequence did not affect basal or IFNγ-induced activity, suggesting that all upstream regulatory sequences were located within bases -1 to -1272 (SEQ ID NO:1).

From all of the constructs tested the inductivity of the pGL3(656) is the highest, indicating that this DNA fragment contains the optimal inducible promoter of IL-18BP.

The results show that the minimal inducible promoter is located 122 bp upstream of the transcription start site (SEQ ID NO:3) containing the IRF-E and GAS elements, wherein the maximal and optimal inducible promoter is located 656 bp upstream of the transcription start site (SEQ ID NO: 2) containing in addition to the IRF-E and GAS elements, two C/EBPβ elements.

Example 7

Involvement of IRF-1 in IL-18BP Expression In-Vivo.

To explore the involvement of IFR-1, the binding site of which was found to be in the promoter of IL-18BP, in IL-18BP expression the expression of IL-18BP in IRF-1 deficient mice was studied.

Figure 6:
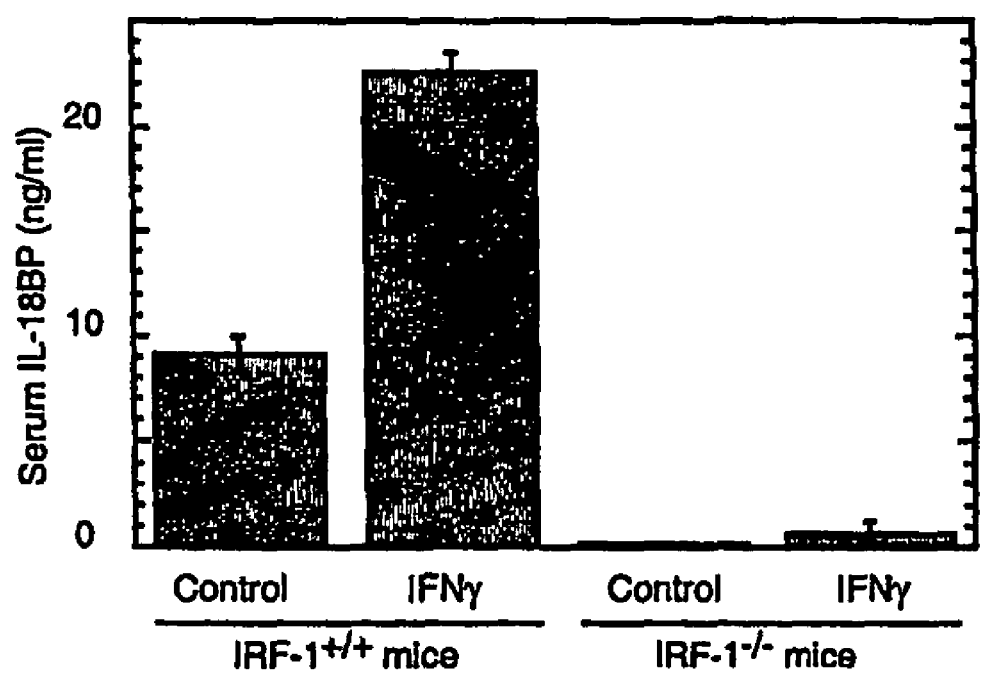
FIG. 6 shows that IRF-1 is essential for IL-18BP expression in mice. Serum IL-18BP of C57B1/6 IRF-1$^{-/-}$ and control C57 B1/6 mice that were injected intraperitoneally with murine IFNγ (53,000 u/mouse). Mice were bled before injection and 24 h post injection. Serum IL-18BP was determined by ELISA. Data are mean±SE (n=6 for each group). The differences between serum IL-18BP in control and IRF-deficient mice, as well as the induction of IL-18BP in control mice were statistically significant (p<0.05).

The levels of IL-18BP were measured in IRF-1-deficient mice (Jackson laboratories, Bar Harbor Me.) before and after administration of murine IFNγ and compared to those in control C57B 1/6 mice (FIG. 6). Basal serum IL-18BP in control C57B1/6 mice was 9.1±1.9 ng/ml and was significantly increased by IFNγ to 22.4±2.2 ng/ml. In contrast, serum IL-18BP in IRF-1-deficient mice was below the limit of detection and increased to only 0.7±1.15 ng/ml with IFNγ. This result confirmed the importance of IRF-1 as a mediator of basal as well as IFNγ-induced expression of IL 18BP.

Example 8

Detection of the Transcription Factors Binding to the IL-18BP Promoter Under Inductive Conditions.

Figure 7:
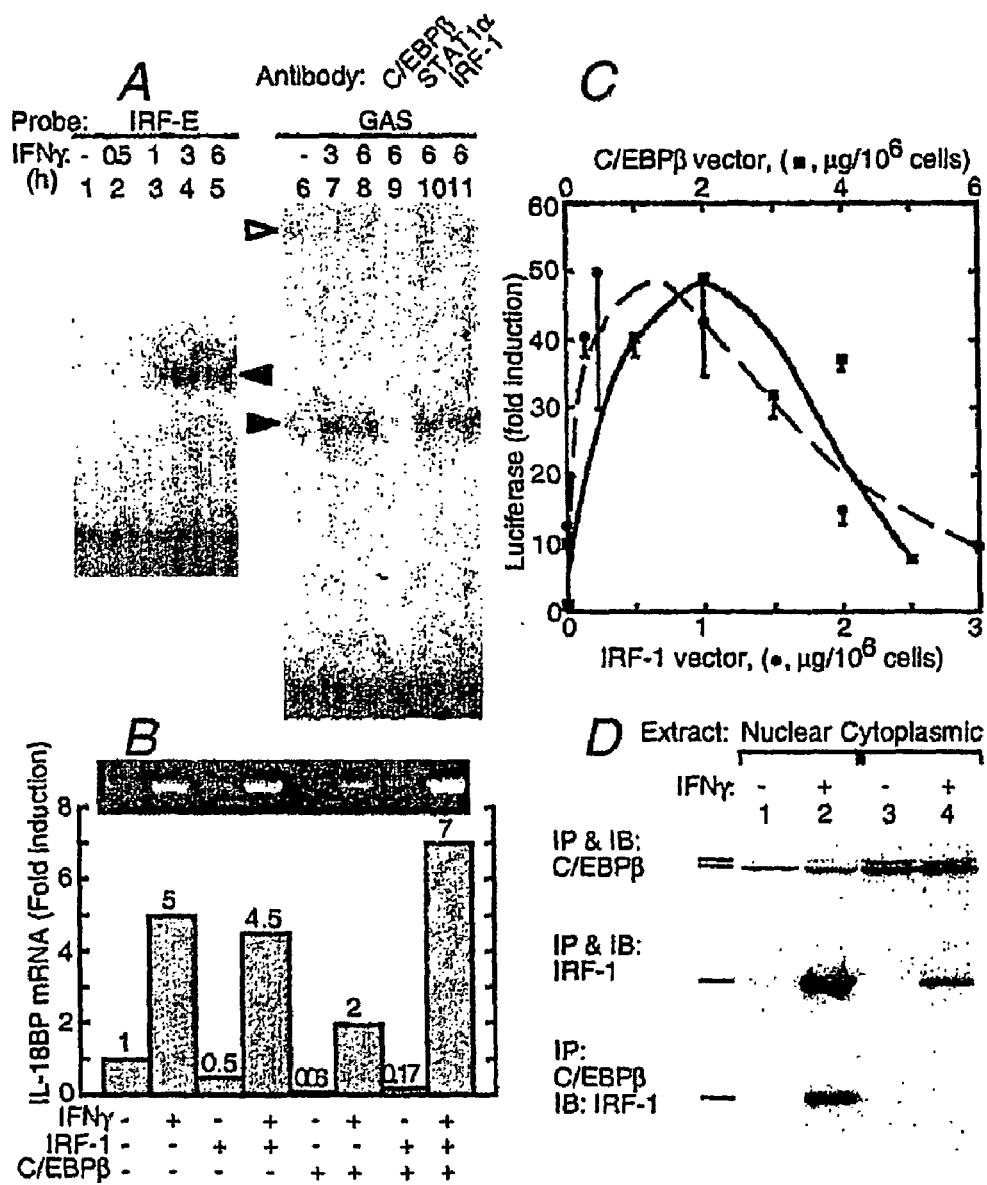
FIG. 7 shows the role of IRF-1 and C/EBPβ in IL-18BP gene induction and their association. (A) electrophoretic mobility shift assay (EMSA Example 18) of dsDNA probes corresponding to bases -33 to -75 (IRF-E, left panel) and -8 to -55 (GAS, right panel). HepG2 cells were treated with IFNγ for the indicated times and nuclear extracts were allowed to react with the IRF-E or GAS probes. Shifted bands are indicated by filled arrowheads. The GAS complex was also subjected to super shift with the indicated antibodies. The super shifted band is indicated by an open arrowhead. (B) semi-quantitative RT-PCR of IL-18BP mRNA from HepG2 cells that were transfected with the indicated combinations of IRF-1 or C/EBPβ expression vectors. Where indicated, IFNγ was added and cells were harvested 5 h later. Values were normalized to β actin mRNA. (C) luciferase activity in cells transfected with the luciferase reporter vector pGL3(1272), containing the complete IL-18BP promoter, together with the indicated concentration of pCDNA3-IRF-1 (circles) and 1 μg/10⁶ cells of pCDNA3-C/EBPβ. Alternatively, cells were transfected with the indicated concentration of pCDNA3-C/EBPβ (squares) and 0.1 μg/10⁶ cells of pCDNA3-IRF-1. Luciferase activity was normalized by the βGal activity. (D) immunoblots of nuclear and cytoplasmic extracts (see Example 17 for preparation of extracts) of cells treated with IFNγ (100 U/ml, 2 h). Extracts were immunoprecipitated (IP) and immunoblotted (IB) with the indicated antibodies.

Electrophoretic mobility shift assays (EMSA Example 18) were employed to identify protein-DNA interactions among the various response elements within the IL-18BP promoter. Labelled ds DNA probes corresponding to bases -33 to -75 (containing the IRF-E) and -8 to -55 (containing the GAS) were allowed to bind with nuclear extracts of control and IFNγ-treated cells. A complex of the IRF-E-containing probe and nuclear protein(s) was apparent following incubation of cells for 1 h with IFNγ and maximal response was seen at 3 h (FIG. 7 A, lanes 1-5). As expected, addition of antibodies to IRF-E caused a "super-shift", whereas control anti-signal transducer and activator of transcription 1 (STAT1) antibodies had no effect (data not shown). In contrast with IRF-E, the GAS-containing probe was constitutively associated with a protein (FIG. 7 A, lane 6) and this complex was enhanced upon induction of cells with IFNγ for 3 to 6 h (lanes 7, 8). GAS is expected to bind the IFNγ-induced STAT1 dimer. Nevertheless, the complex was not affected by antibodies to STAT1 (lane 10), suggesting that the IFNγ-induced STAT1 dimer was not associated with this GAS. The same negative result was obtained with nuclear extracts of cells treated with IFNγ for only 15 or 30 min (data not shown). Surprisingly, this complex was abolished by antibodies to C/EBPβ (lane 9) and was super shifted with antibodies to IRF-1 (lane 10). Hence the GAS-containing DNA probe appears to bind C/EBPβ despite lack of a consensus C/EBPβ E.

The results obtained with EMSA indicate that upon induction with IFNγ, IRF-1 binds to the IRF-E element in the IL-18BP promoter. In addition, a complex comprising IRF-1 and C/EBPβ is formed and binds to the GAS element.

Example 9

Exploring the Role of the IRF-1-C/EBPβ Complex in IL-18BP Induction.

To further study the role of IRF-1 and C/EBPβ in IL-18BP gene induction, IL 18BPa mRNA was measured by semi-quantitative PT-PCR following overexpression of IRF-1 and C/EBPβ by employing transfection of expression vectors (Example 14, FIG. 7 B). Over-expression of either transcription factor or a combination of both factors in HepG2 cells did not induce IL-18BP mRNA. This result suggested that additional IFNγ-induced factors are required for activation of the IL-18BP gene. Transfection of the cells with either one of the expression vectors followed by their induction with IFNγ actually reduced IL-18BP mRNA compared with IFNγ alone. In contrast, co-expression of the two transcription factors increased the induction of IL-18BP mRNA by IFNγ. This result suggested that IRF-1 and C/EBPβ must be present at a certain ratio, possibly forming a complex within the transcription initiation complex. To further study the possible interaction between IRF-1 and C/EBPβ a titration of luciferase activity by co-transfecting cells with pGL3 (1272), a fixed amount of an IRF-1 expression vector and varying amounts of C/EBPβ expression vector was performed. Similarly, luciferase activity when the C/EBPβ vector was kept constant and with varying amounts of the IRF-1 vector was measured. In both cases a bell-shaped dose-response curve was obtained, suggesting that optimal IL-18BP induction requires a fixed molar ratio between these two transcription factors (FIG. 7 C).

Immunoprecipitation studies were carried out in order to confirm the physical association between IRF-1 and C/EBPβ (Example 19, FIG. 7 D). Immunoprecipitation (ip) followed by immunoblotting (ib) of nuclear and cytoplasmic proteins (Example 15) from IFNγ-treated cells with antibodies to C/EBPβ revealed that C/EBPβ is constitutively expressed in HepG2 cells and translocates to the nucleus in response to IFNγ (upper panel). In contrast to C/EBPβ which is not induced by IFNγ, ip and ib of cell extracts with antibodies to IRF-1 revealed that IFNγ induces the expression of IRF-1. But similar to C/EBPβ, upon IFNγ induction, IRF-1 is translocated to the nucleus (middle panel). Ip with antibodies to C/EBPβ, followed by ib with antibodies to IRF-1 revealed the presence of a stable IRF-1-C/EBPβ complex in the nuclear fraction (lower panel). These results confirm the formation of the IRF-1-C/EBPβ complex upon IFNγ induction and is the first demonstration of the existence of such a complex between these two transcription factors. Thus upon IFNγ induction, the proximal GAS-containing sequence and its adjacent IRF-E bind the complex of C/EBPβ and IRF-1.

Example 10

Exploring the Role of the C/EBP-Es in the IL-18BP Promoter Activity.

Figure 8:
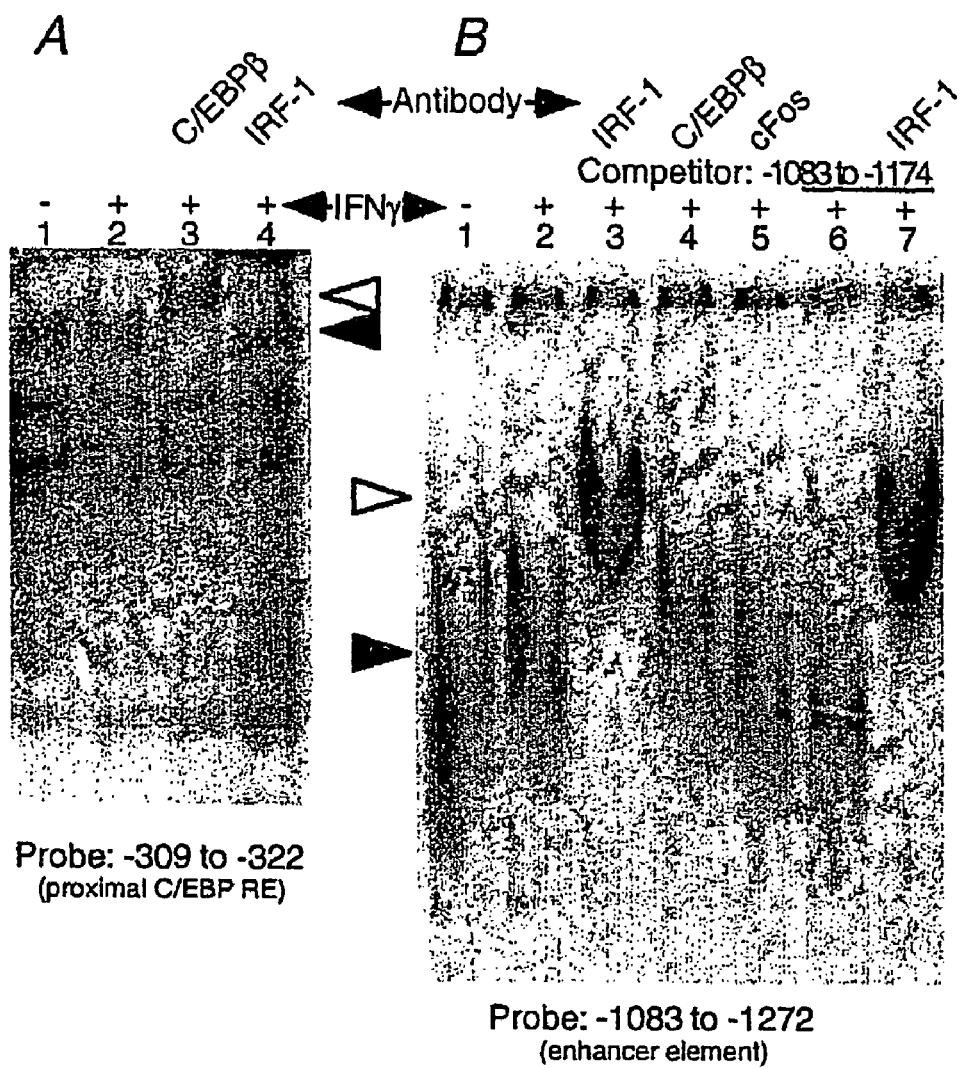
FIG. 8 shows the factors binding to the promoter of IL-18BP upon IFNγ induction (A) EMSA with the proximal C/EBPβ E and whole cell extracts following treatment with IFNγ. Where indicated, the extracts were super shifted with the indicated antibodies. (B) EMSA with a probe corresponding to the distal enhancer and whole cell extracts following treatment with IFNγ. Where indicated, the extracts were super shifted with the indicated antibodies, with or without competition with ds DNA corresponding to the proximal half of the probe. Shifted bands are indicated by filled arrowheads and super shifted band are indicated by open arrowheads.

The two C/EBPβ sites at positions -309 to -322 and -621 to -634 do not have an adjacent IRF-E. Indeed, EMSA (Example 18) of a probe corresponding to the C/EBPβ sites at positions -309 to -322 revealed a retarded band (filled arrowhead) that was super shifted with antibodies to C/EBPβ (open arrowhead) but not with antibodies to IRF-1 (FIG. 8 A). Hence, it was concluded that this site binds C/EBPβ and not its complex with IRF-1. Furthermore, this band was generated with a nuclear extract of un-induced HepG2 cells that constitutively express C/EBPβ but lack IRP-1. In fact, IFNγ did not increase the expression of C/EBPβ in these cells (FIG. 8 D) and consequently it did not increase the intensity of the retarded band (FIG. 8 A). Similar results were obtained with the more distal C/EBPβ site (data not shown).

The results show that the C/EBP transcription factor unlike the IRF-1, is constitutively expressed and not induced by IFNγ and that in addition of binding to IRF-1 and to GAS, it binds to both of the C/EBP elements present in the IL-18BP promoter.

Example 11

Studying the Role of the Enhancer in the Expression of IL-18BP.

The regulatory role of the distal enhancer was studied by EMSA (Example 18) with a 192 bp DNA probe, corresponding to nucleotides -1081 to -1272. Nuclear extract of control HepG2 cells formed a complex with this probe (FIG. 8 B, filled arrowhead). Upon treatment of the cells with IFNγ, the complex was more intense and somewhat more retarded. A super-shift of this complex with antibodies directed against IRP-1, C/EBPβ and cFos was then performed. Of these, only anti IRF-1 elicited a super-shift (FIG. 8 B, empty arrowhead). An unlabelled dsDNA corresponding to nucleotides -1083 to -1174 did not compete with the radiolabeled probe, indicating that the nuclear proteins were bound to residues -1175 to -1272. Since IRF-E was identified only in the proximal region, this result suggests that the distal enhancer was probably associated with the proximal IRF-E.

These results indicate that the distal enhancer interacts with the basal promoter through IRF-1.

Example 12

ELISA for IL-18BP.

Human IL-18BP was measured by a double antibody ELISA as described (Novick et al 2001). Mouse IL-18BP was measured by a double antibody ELISA using rabbit antigen affinity-purified polyclonal antibody to murine IL-18BP and biotinylated antibody that were obtained from Cytolab, Israel.

Example 13

RNA Isolation and Reverse Transcription (RT)-PCR.

Following treatment in serum-free medium, HepG2, and WISH cells ($10^6$) were harvested at the indicated times and total RNA was extracted using TRI reagent. cDNA was prepared using random hexamers and SuperscriptII (Invitrogen™, Leek, The Netherlands) according to the manufacturer's instructions. PCR was performed with the following primers: human IL-18BP, 5' CACGTCGTCACTCTCCTGG and 5' CGACGTGACGCTGGACAAC; human IRF-1 5' GACCCTGGCTAGAGATGCAG and 5' GAGCTGCT-GAGTCCATCAG; human βActin 5' GTGGGGCGC-CCCAGGCACCA and 5' CTCCTTAATGTCACGCAC-GATTTC. Amplifications were done by initial denaturation (92° C., 2 min), 28 cycles of denaturation (92° C., 45 sec.), annealing (62° C., 1 min) and extension (72° C., 1.5 min), and final extension (72° C., 10 min). The resulting PCR products were resolved by agarose (1%) gel electrophoresis.

Example 14

Rapid Amplification of 5' cDNA Ends (5' RACE).

5' RACE was performed with a 5' RACE System (GIBCO BRL) according to the manufacturer's instructions. Briefly, total RNA from IFNγ-treated WISH cells was reverse-transcribed (Example 13) with a primer complementary to nucleotides 89-70 of IL-18BPa mRNA (GenBank Accession No. AF110799) followed by tailing of the newly synthesized ends with an anchor DNA. PCR was then performed with a forward primer complementary to the anchor DNA and a nested reverse primer complementary to nucleotides 31-11 of IL-18BPa mRNA. The PCR products were then subcloned and subjected to DNA sequence analysis.

Example 15

Plasmids and Cloning.

The entire putative IL-18BPa promoter region of 1601 bp was obtained by PCR of genomic DNA using a sense primer (S4753.pgl) containing a Kpn I site (5' CTATATGGTAC-CCACCCTTCCTTTTACTTTTTCC) and reverse primer (R1exA) containing Nhe I site (5' TATCGCTAGCCAGTCA-CACAGGGAGGCAGT). The PCR product was cloned into pGEM-T Easy vector (Promega, Madison, Wis.) and verified by DNA sequence analysis. A Kpn I-Nhe I fragment was isolated from the pGEM-T Easy clone and ligated into pGL3-Basic vector (Promega) using Rapid DNA Ligation Kit (Roche) to give pGL3(1601). A series of 5'-truncated reporters (pGL3(1454), pGL3(1274), pGL3(1106), pGL3(656), pGL3(280) and pGL3(122) was similarly prepared with the same reverse primer and with the following sense primers, respectively:

```
S334.pgl   5': CTATATGGTACCCATGAACTAGACACCTAGAG;

S415.pgl   5': CTATATGGTACCCTACAAGAAGTTTGAGATCA;

S501.pgl   5': CTATATGGTACCCAGCCGTTGCACCCTCCCAATCAC;

1exD pgl   5' CTATATGGTACCGTCTTGGAGCTCCTAGAGG;

S504.pgl   5' CTATATGGTACCCACCAAAGTCCTGACACTTG
and

S139.pgl   5' TTGGTACCCACTGAACTTTGGCTAAAGC..
```

All PCR products were also cloned into pGL3-Basic vector in the opposite orientation to serve as controls.

Example 16

Transient Transfection Assays.

HepG2 or WISH cells in 6 well plates ($0.5 \times 10^6$/well) were transfected using FuGENE 6 and the indicated luciferase reporter vector (0.5 µg/well) and pSV40 βGAL (0.2 µg/well, Promega) according to manufacturer's instructions. In some cases co-transfection was done with the following expression vectors: poDNA3-IRF-1 (0.07-1.5 µg/well, kindly provided by Dr. B. Levy, Technion, Israel); pcDNA3-C/EBPβ (0.5-2.5 µg/-well, kindly provided by Dr. D. Zipori, Weizmann Institute of Science). After 16 h cells were treated with either IFNγ

(100 U/ml), IL-6 (150 U/ml), TNFα (10 ng/ml) or their indicated combinations in serum-free medium for 24 h. Cells were then collected, lysed and Luciferase activity was measured. All results were normalized against β-galactosidase activity, Example 17

Preparation of Nuclear and Cytoplasmic Extracts.

Cells were washed 3×with ice-cold phosphate buffered saline (PBS) and immediately frozen in liquid nitrogen. Cell pellets were re-suspended in four packed cell volume of cytoplasmic buffer (10 mM Hepes, pH 7.9, 10 mM NaCl, 0.1 mM EDTA, 5% (by vol.) glycerol, 1.5 mM $MgCl_2$, 1 mM dithiothreitol (DTT), 0.5 mM PMSF, 50 mM NaF, 0.1 mM $Na_3VO_4$, 2 mM EGTA, 10 mM EDTA, 10 mM $Na_2MoO_4$, 2 μg/ml each of leupeptin, pepstatin and aprotinin). The lysate was centrifuged (3000×g, 10 min.) and the supernatant containing the cytoplasmic proteins was collected. The pellet was re-suspended in 2.5 packed cell volumes of nuclear buffer (identical to cytoplasmic buffer except that NaCl was increased to 0.42 M). Nuclear debris was removed by centrifugation (15,000× g, 20 min. 4° C.), aliquots of the supernatant were frozen in liquid nitrogen and stored at −80° C. Protein concentration was determined by a BCA Protein assay reagent kit (Pierce, Rockford USA) using bovine serum albumin as a standard.

Example 18

Electrophoretic Mobility Shift Assays.

Ds oligonucleotides corresponding to selected response elements (10 pmol) were labeled with [$^{32}$P]3 ATP by polynucleotide kinase (New England Biolabs). Nuclear extracts (5 μg protein) were pre-incubated (15 min., 0° C.) together with poly(dI-dC) (Amersham Pharmacia biotechnology) in 20 μl-EMSA Buffer (20 mM Hepes pH 7.5; 5 mM $MgCl_2$, 2 mM EDTA, 5 mM DTT and 5% (by vol.) glycerol). A labeled probe (3×10$^4$ cpm) was then added and incubation continued for an additional 30 min. at room temperature. For super-shift assays samples were incubated with the indicated antibodies (4 μg, 1 h at 0° C.) prior to addition of the probe. A 200 fold excess of wild type and mutated competitors were added together with the relevant probe. Reaction mixtures were then electrophoresed in 5% non-denaturing polyacrylamide gels. Gels were vacuum dried and autoradiographed overnight at −80° C.

Example 19

Immunoprecipitation (ip) and Immunoblot (ib) Analysis.

Nuclear or cytoplasmic protein extracts (80 μg) were incubated with 6 μg of the indicated polyclonal antibodies overnight at 4° C. and immunoprecipitated with Protein G Sepharose beads (Pharmacia) for 1 h at room temperature. The beads were then boiled in SDS-PAGE sample buffer containing 10% DTT and the supernatant resolved by SDS-PAGE (10% acrylamide) under reducing conditions. The gel was then blotted onto a nitrocellulose membrane and proteins detected with the indicated antibodies. Immune complexes were identified by Super Signal™ (Pierce) detection kit.

Example 20

Preparation of CHO r-hsLDLR Using the IL-18BP Promoter.

Stable recombinant CHO cells expressing human soluble LDLR are generated by co-transfection of CHO-DUKX cells lacking the dihydrofolate reductase (DHFR) gene (Urlaub, G. et al., 1980) with two expression vectors: one containing the N-terminal ligand-binding domain of the LDLR, beginning at amino acid residue Asp (+4) up to Glu 291 (+291), and pDHFR, containing the murine gene for DHFR, DHFR controlled by the early SV40 promoter and sLDLR gene by the IL-18BP promoter (SEQ ID NO:2) and transcription termination elements of the SV40 early region. Transfection is performed by cationic liposomes using LipofectAmine (Gibco BRL), according to the protocol described by the manufacturer. Seventy-two hours after transfection cells are transferred to a selective medium lacking deoxy and ribonucleosides and supplemented with 10% dialysed FCS. Cells expressing DHFR activity are able to form colonies, which are isolated by lifting the cells with trypsin-soaked paper discs The cells are grown and screened for r-hsLDLR activity. The transfected cells are then subjected to gene amplification by MIX, followed by subcloning and selection of the stable producer clones.

REFERENCES

Bahner 1993 J Virol 67:3199.
Breni et al. 1992 Blood 80:1418.
Boshart et al. 1985 Cell 41:521.
Brinster et al. (1981) Cell 27:233.
Cassel 1993 Exp Hematol. 21:585.
Chao 1993 Blood 81:2031.
Chen 1997 Nat Med 3:1110
Costantini et al. (1981) Nature 294:982
Couture 1996 Trends Genet 12:510.
Dignam et al. 1983 Nucleic Acid Res. 11:1475
Dijkema et al. 1985 EMBO J 4:761.
Dunbar 1995Blood 85: 3048.
Dynan and Tjian 1985 Nature 316:774.
Dynan W 1989 Cell 58:1-4.
Fletcher et al. 1987 Cell 51:773-781.
Fried et al. 1981 Nucleic Acids Res. 9, 6505
Gale et al. 1992 Transplant 9:151.
Gordon et al. (1976) PNAS 73:1260.
Gorman et al 1982b PNAS 79:6777
Henon et al. 1992 Transplant 9:285.
Herzog, R. W., Hagstrom, J. N., Kung, S. H., Tai, S. J., Wilson, J. M., Fisher, K. J. & High, K. A. (1997) *Proc. Natl. Acad. Sci. USA* 94, 5804-5809
Harpers et al. (1981) Nature 293:540.
Hao et al. 1995 Blood 86:3745.
Junker 1997 Blood 89:4299.
Kearns 1997 Human Gene Ther 8:310.
Kohn et al. (1999) Blood 94:368.
Lee 1994 J. Virol 68:8254
Lili Wang*, Kazuaki Takabe†, Scott M. Bidlingmaier‡, Charles R. III‡, and Inder M. Verma* Vol. 96, Issue 7, 3906-3910, Mar. 30, 1999 Sustained correction of bleeding disorder in hemophilia B mice by gene therapy
Lotti et al. 2002 J of Virol. 76:3996.
Malim 1989 Cell 58:205.
Maniatis et al 1987 Science 236:1237.
Marasco 1997 Gene Ther 4:11.

Muhl, H., Kampfer, H., Bosmann, M., Frank, S., Radeke, H. & Pfeilschifter, J. (2000) *Biochem. Biophys. Res. Commun.* 267, 960-963.

Murphy, J. E., Zhou, S., Giese, K., Williams, L. T., Escobedo, J. A. & Dwarki, V. J. (1997) *Proc. Natl. Acad. Sci. USA* 94, 13921-13926

Neighbors, M., Xu, X., Barrat, F. J., Ruuls, S. R., Churakova, T., Debets, R., Bazan, J. F., Kastelein, R. A., Abrams, J. S. & O'Garra, A. (2001) *J. Exp. Med.* 194, 343-354.

Novick, D., Schwartsburd, B., Pinkus, R., Suissa, D., Belzer, I., Sthoeger, Z., Keane, W. F., Chvatchko, Y., Kim, S. H., Fantuzzi, G., Dinarello, C. A. & Rubinstein, M. (2001) *Cytokine* 14, 334-342.

Novick D, Kim S H, Fantuzzi G, Reznikov L L, Dinarello CA, Rubinstein M. Immunity 1999 January; 10(1):127-36

Novick D, Schwartsburd B, Pinkus R, Suissa D, Belzer I, Sthoeger Z, Keane W F, Chvatchko Y, Kim S H, Fantuzzi G, Dinarello C A, Rubinstein M. Cytokine 2001 Jun. 21; 14(6):334-42

McKnight and Tjian 1986 Cell 46:795.

Mioshi et al. 1999 Science 283:682.

Moritz 1993 J Exp Med 178:529.

Palmiter et al. 1986 Ann Rev. Genet. 20:465.

Revzin 1989 Biotechniques 7:346

Sassone-Corsi and Borreli 1986 Trends Genet 2:215

Scheidereit et al. 1987 Cell 51:783-793.

Slobod 1996 Blood 88, 3329

Snyder, R. O., Miao, C. H., Patijn, G. A., Spratt, S. K., Danos, O., Nagy, D., Gown, A. M., Winther, B., Meuse, L., Cohen, L. K., et al. (1997) *Nat. Genet.* 16, 270-276

Snyder, R. O., Miao, C., Meuse, L., Tubb, J., Donahue, B. A., Lin, H. F., Stafford, D. W., Patel, S., Thompson, A. R., Nichols, T., et al. (1999) *Nat. Med.* 5, 64-70

Song, S., Morgan, M., Ellis, T., Poirier, A., Chesnut, K, Wang, J., Brantly, M., Muzyczka, N., Byrne, B. J., Atkinson, M., et al. (1998) *Proc. Natl. Acad. Sci. USA* 95, 14384-14388

Sullenger 1990 Cell 63:601.

Veres et al. 1996 J Virol 70:8792

Verma et al. 1997 Nature 389:239.

Voss et al., 1986 Trends Biochem Sci. 11:287.

Wagner et al. (1981) PNAS 78:5016

Xiao, W., Berta, S. C., Lu, M. M., Moscioni, A. D., Tazelaar, J. & Wilson, J. M. (1998) *J. Virol.* 72, 10222-10226

Zecchina G, Novick D, Rubinstein M, Barak V, Dinarello C, Nagler A. J Hematother Stem Cell Res. 2001 December; 10(6):769-76.

Zhou 1994 Gene 149:33.

Zweibel et al. 1989 Science 243:220.

---

The invention claimed is:

1. An isolated DNA sequence comprising a functional human IL-18BP promoter sequence comprising the nucleotide sequence of SEQ ID NO: 1 and further comprising SEQ ID NO: 5 operably linked to the 3' end of SEQ ID NO:1.

2. The isolated DNA sequence according to claim 1, operably linked to an intron.

3. The isolated DNA sequence according to claim 2, wherein the intron consists of the first intron of IL-18BP.

4. The isolated DNA sequence according to claim 1, further comprising a gene operatively linked to the isolated DNA sequence.

5. The isolated DNA sequence according to claim 4, wherein the gene encodes IL-18BP.

6. The isolated DNA sequence according to claim 4, wherein the gene encodes a heterologous protein.

7. The isolated DNA sequence according to claim 6, wherein the heterologous protein is a luciferase protein.

8. The isolated DNA sequence according to claim 6, wherein the heterologous gene encodes a protein selected from an interferon-beta, a TNF, an erythropoietin, a tissue plasminogen activator, a granulocyte colony stimulating factor, a manganese-superoxide 41 dismutase, an immunoglobulin, an immunoglobulin fragment, a growth hormone, an FSH, an hCG, an IL-18, an hsLDLR and a TNF receptor binding protein.

9. A vector comprising the DNA sequence according to claim 1.

10. An isolated host cell comprising the vector according to claim 9.

11. The isolated host cell according to claim 10, which is a mammalian cell.

12. The isolated host cell according to claim 11, selected from the group consisting of CHO, WISH, HepG2, Cos, CV-1.HeLA, and Hakat U937 cells.

13. A recombinant virus vector which comprises a portion of the virus genomic nucleic acid, a DNA fragment comprising a gene of interest and a DNA fragment comprising the DNA sequence according to claim 1, operably linked to the gene of interest.

14. The recombinant virus vector according to claim 13, wherein the gene of interest encodes a protein selected from an interferon-beta, a TNF, an erythropoietin, a tissue plasminogen activator, a granulocyte colony stimulating factor, a manganese-superoxide dismutase, an immunoglobulin, an immunoglobulin fragment, a growth hormone, an FSH, an hCG, an IL-18, an hsLDLR and a TNF receptor binding protein.

15. The recombinant virus vector according to claim 13, wherein the virus is an adeno-associated virus.

16. A pharmaceutical composition comprising the isolated DNA sequence of claim 1.

17. An isolated DNA sequence comprising a functional human IL-18BP promoter comprising the nucleotide sequence of SEQ ID NO: 1 and further comprising SEQ ID NO: 5 operably linked to the 3' end of SEQ ID NO:1 and wherein the promoter is mutated at one or more AP1 sites present in the silencer element present in SEQ ID NO: 1.

18. The isolated DNA sequence according to claim 17, further comprising an intron.

19. The isolated DNA sequence according to claim 18, wherein the intron consists of the first intron of IL-18BP.

20. The isolated DNA sequence according to claim 17, further comprising a gene operatively linked to the isolated DNA sequence.

21. The isolated DNA sequence according to claim 20, wherein the gene encodes IL-18BP.

22. The isolated DNA sequence according to claim 20, wherein the gene encodes a heterologous protein.

23. The isolated DNA sequence according to claim 22, wherein the heterologous protein is a luciferase protein.

24. The isolated DNA sequence according to claim 22, wherein the heterologous gene encodes a protein selected from an interferon-beta, a TNF, an erythropoietin, a tissue plasminogen activator, a granulocyte colony stimulating factor, a manganese-superoxide 41 dismutase, an immunoglobulin, or a fragment thereof, a growth hormone, an FSH, an hCG, an IL-18, an hsLDLR and a TNF receptor binding proteins.

25. A vector comprising the DNA sequence according to claim 17.

26. An isolated host cell comprising the vector according to claim 25.

27. The isolated host cell according to claim 26, which is a mammalian cell.

28. The isolated host cell according to claim 27, selected from the group consisting of CHO, WISH, HepG2, Cos, CV-1.HeLA, and Hakat U937 cells.

29. A recombinant virus vector which comprises a portion of the virus genomic nucleic acid, a DNA fragment comprising a gene of interest and a DNA fragment comprising the DNA sequence according to claim 17, operably linked to the gene of interest.

30. The recombinant virus vector according to claim 29, wherein the gene of interest encodes a protein selected from an interferon-beta, a TNF, an erythropoietin, a tissue plasminogen activator, a granulocyte colony stimulating factor, a manganese-superoxide dismutase, an immunoglobulin, an immunoglobulin fragment, a growth hormone, an FSH, an hCG, an IL-18, an hsLDLR and a TNF receptor binding protein.

31. The recombinant virus vector according to claim 29, wherein the virus is an adeno-associated virus.

32. A pharmaceutical composition comprising the isolated DNA sequence of claim 17.

* * * * *